United States Patent
Cinqualbre et al.

(10) Patent No.: US 11,437,124 B2
(45) Date of Patent: Sep. 6, 2022

(54) METHOD FOR PROCESSING, SHAPING, PRESENTATION AND OPTIMIZED DISPLAY OF RESULTS OF BIOLOGICAL ANALYSES BASED ON CONSOLIDATED HEALTH DATA AND NORMALIZED VALUES

(71) Applicant: HOPI MEDICAL, Rosheim (FR)

(72) Inventors: Jacques Cinqualbre, Rosheim (FR); Damien Uhlrich, Saint Nicolas de Port (FR)

(73) Assignee: HOPI MEDICAL, Rosheim (FR)

( * ) Notice: Subject to any disclaimer, the term of this patent is extended or adjusted under 35 U.S.C. 154(b) by 1094 days.

(21) Appl. No.: 16/068,799

(22) PCT Filed: Jan. 6, 2017

(86) PCT No.: PCT/FR2017/050039
§ 371 (c)(1),
(2) Date: Dec. 17, 2018

(87) PCT Pub. No.: WO2017/118826
PCT Pub. Date: Jul. 13, 2017

(65) Prior Publication Data
US 2019/0095580 A1 Mar. 28, 2019

(30) Foreign Application Priority Data
Jan. 8, 2016 (FR) ...................................... 1650163

(51) Int. Cl.
| | |
|---|---|
| G16H 10/40 | (2018.01) |
| G06Q 10/10 | (2012.01) |
| G16H 50/50 | (2018.01) |
| G16B 40/00 | (2019.01) |
| G16B 45/00 | (2019.01) |
| G16B 25/00 | (2019.01) |
| G16B 50/00 | (2019.01) |
| G06F 17/18 | (2006.01) |

(52) U.S. Cl.
CPC ............. *G16H 10/40* (2018.01); *G06F 17/18* (2013.01); *G06Q 10/10* (2013.01); *G16B 25/00* (2019.02); *G16B 40/00* (2019.02); *G16B 45/00* (2019.02); *G16B 50/00* (2019.02); *G16H 50/50* (2018.01)

(58) Field of Classification Search
None
See application file for complete search history.

(56) References Cited

U.S. PATENT DOCUMENTS

| 8,688,476 B2 | 4/2014 | Cinqualbre et al. |
| 2006/0085515 A1 | 4/2006 | Kurtz et al. |

OTHER PUBLICATIONS

Vesterinen, H. M., et al. "Meta-analysis of data from animal studies: a practical guide." Journal of neuroscience methods 221 (2014): 92-102.*
Marc D. Silverstein; "An Approach to Medical Errors and Patient Safety in Laboratory Services;" Centers for Disease Control and Prevention; Quality Institute Meeting: Making the Laboratory a Partner in Patient Safety; Atlanta, GA, Apr. 8, 2003 (22 pages).
Eric S. Lander; "Brave New Genome;" The New England Journal of Medicine; vol. 373; Issue 1; Jul. 2, 2015; pp. 5-8 (4 pages).
Bayer et al.; "Public Health in the Precision-Medicine Era;" The New England Journal of Medicine; vol. 373; Issue 6; Aug. 6, 2015; pp. 499-501 (3 pages).
Hunter et al.; "Let's Not Put All Our Eggs in One Basket;" The New England Journal of Medicine; vol. 373; Issue 8; Aug. 20, 2015; pp. 691-693 (3 pages).
Hyman et al.; "Vermurafenib in Multiple Nonmelanoma Cancers with BRAF V600 Mutations;" The New England Journal of Medicine; vol. 373; Issue 8; Aug. 20, 2015; pp. 726-736 (11 pages).
"Blink design library: Quick Item Details;" Apr. 3, 2008; pp. 1-3; XP055202180; Retrieved from the Internet: URL: http://web.archive.org/web/20080403235803/http://designlibrary.blinkinteractive.com/2006/10/quick_item_deta.html (3 pages).
International Search Report issued in PCT/FR2017/050039 dated Apr. 12, 2017 (5 pages).
Written Opinion of the International Searching Authority issued in PCT/FR2017/050039 dated Apr. 12, 2017 (5 pages).

* cited by examiner

*Primary Examiner* — G Steven Vanni
(74) *Attorney, Agent, or Firm* — Osha Bergman Watanabe & Burton LLP

(57) ABSTRACT

A method for tracking a biological parameter of a patient by processing one or more initially-measured values A(n) that correspond to results of one or more biological analyses of the patient's biological parameter from one or more laboratories, may include receiving data from one or more laboratories that includes at least one initial value A(n) and metadata indicating a corresponding normal range. The data is recorded and each of the initial values A(n) are transformed into a normalized value Anorm(n) through the use of a mathematical model and computer processing. A progression over time of the given biological parameter may be generated and displayed using a method of electronic graphical representation, wherein the normalized values Anorm(n) may be presented in combination with at least one element of data that relates to a common normalized normal range.

13 Claims, 15 Drawing Sheets

| BLOOD BIOCHEMISTRY | | |
|---|---|---|
| UREA<br>(Beckman urease spectrophotometry) | 0.52 g/l<br>8.68 mmol/l | (0.17-0.43)<br>(2.84-7.18) |
| CREATININE<br>(Beckman creatininase, IDMS enzymatic method) | 9.5 mg/l<br>84.1 umol/l | (7.2-11.8)<br>(63.7-104.4) |

FIG. 1a

| BIOCHEMISTRY | | Normal Values |
|---|---|---|
| UREA ------------------------<br>Urease kinetic method - GLDH Cobas Mira Plus | 0.52 g/l<br>8.63 mmol/l | 0.20 to 0.50<br>3.32 to 8.30 |
| CREATININE ------------------<br>Jaffe Cobas Mira Plus kinetic method | 9.2 mg/l<br>81.4 umol/l | 5.0 to 13.0<br>44.2 to 115.1 |

FIG. 1b

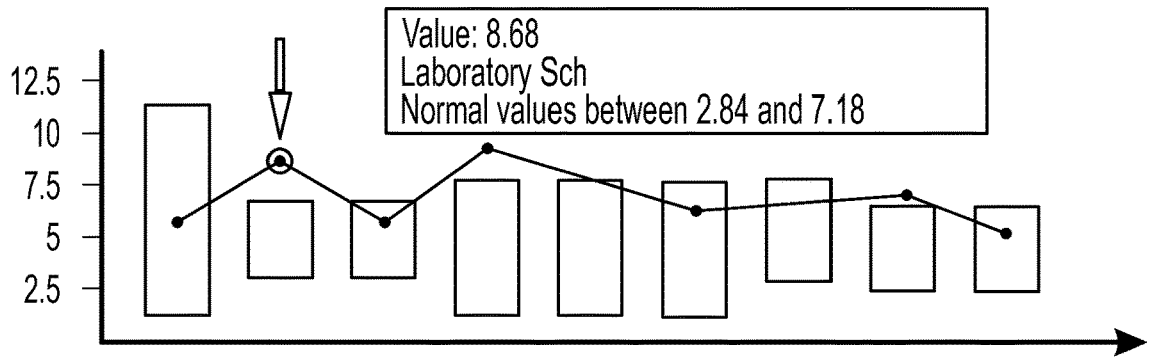
FIG. 3a
FIG. 3b
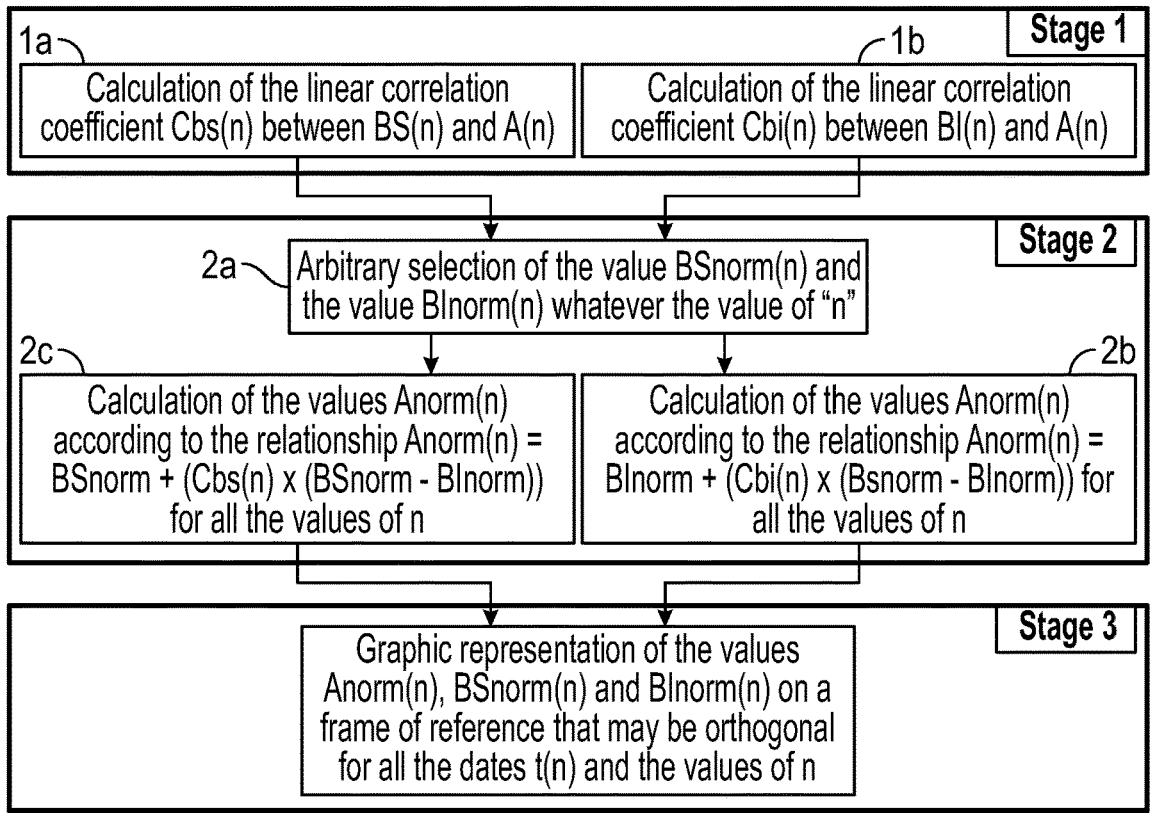
FIG. 4

METHOD FOR PROCESSING, SHAPING, PRESENTATION AND OPTIMIZED DISPLAY OF RESULTS OF BIOLOGICAL ANALYSES BASED ON CONSOLIDATED HEALTH DATA AND NORMALIZED VALUES

TECHNICAL FIELD

The present invention relates to the general technical field of the biological analyses of a patient, used in the medical sector.

Practice of medicine essentially consists of acquiring, interpreting, integrating and ultimately transmitting data in order to improve knowledge of the case to be treated. One can appreciate the importance of managing an electronic medical record that collects, throughout an individual's life, all his/her medical data and makes the latter accessible, at any time and in any place, to any designated and legitimate caregiver to enable him/her to take timely cognizance thereof, in order to assist him/her in his/her medical, diagnostic or therapeutic decisions. This is the whole point of a personal electronic medical record (PEMR), centred and focused on the individual.

The importance of biology in medicine is obvious.

The duty of such a record is to collect together, schematically and in various forms, three types of data: i) clinical, ii) biological and iii) imaging.

The clinical data, obtained from the practitioner's observations and thoughts, are essential but extremely subjective and operator-dependent.

Imaging data are perfectly objective and factual, but late in arrival, since they indicate a declared disease.

Biology therefore appears to be the essential component, since it is involved in making 70% of medical decisions*.

* source: Marc Silverstein, Centers for Disease Control, Atlanta Ga., April 2003: "An approach to medical errors and patient safety in laboratory services" in "Henry's Clinical diagnosis and management by laboratory methods" 22nd Edition Saunders, Elsevier.

Biology is the most frequently performed additional examination (more than 7 billion tests per year in the USA and more than 500 million in France), sometimes even outside any context of disease. One of every 6 medical consultations results in prescription of biological tests.

As the most readable medical data, biology is a powerful indicator of health since it summarises and adds up
i) the effects (achieved or being achieved) of our genetic predispositions,
ii) behavioural aspects specific to the individual, either protective or harmful, which are the consequences of a virtuous personal attitude of prevention or, conversely, of an addiction,
iii) the possible consequences of external influences (attacks suffered actively or passively, accidentally, due to the environment, etc.) and finally,
iv) the inevitable effects of advanced age.

Biology forms the cornerstone of the personal electronic medical record. It forms the latter's framework to which textual records and imaging files are attached in a continuous chronological fashion. This record is called "personal", since it is simultaneously:
the focal point of the medical data,
the reference centre for the various healthcare professionals who are allowed to manage this unique patient record and the sole property of the person in question;
In this respect, it is independent from or linked to the records of the healthcare professionals, depending on the individual's choice and in compliance with the currently applicable legal provisions.

Biology is essential for caring for people. It provides other indirect benefits however: it sheds light on new data arising from genome sequencing or from identification of tissue groups that announce predispositions to certain diseases but remain, more often than not, silent regarding the probability of fulfilling said predisposition ("*Brave new genome*» E. S. Lander, NEJM, 2015, 373, 5-8; *"Public Health in the Precision-Medicine era"* R. Bayer, S. Galea, NEJM, 2015, 373, 499-501).

Other examples include development of therapeutic strategies based on analysis of massive data, particularly within the context of individualised medicine, precision medicine or totally personalised medicine. At a time when personalised therapies lead to institution of anti-cancer treatments not based on tumour location but on subclassifications based solely on genetic mutations (regardless of the "nature" and location of the tumour), knowledge of the individual's longitudinal biological follow-up will make it its own witness for assessing therapeutic efficacy, without resorting to comparisons that have become impossible according to the conventional methods of clinical studies (*"Let's not put all our eggs in one basket"* D J Hunter, R B d'Agostino, NEJM, 2015, 373, 691-693; *"Vermurafenib in multiple nonmelanoma cancers with BRAF V600 mutation"* D M Hyman and others, NEJM, 2015, 373, 726-736), However, massive data are difficult to acquire in medicine for a series of reasons among which the technical and ethical dimensions occupy a forefront position. Biology is the most abundant source, with legitimate respect for and protection of anonymity.

The medical significance of a biological test should be properly understood.

A test provides an initial answer depending on whether or not the measured value falls within the normal range, the latter being synonymous with a pathological situation, either by excess or by default. This raises the fundamental question of determining this so-called normal range.

Currently, in theory, the reference values for medical biology tests are determined on the basis of examinations performed in healthy subjects, considered collectively or distributed by age groups and according to other criteria: gender, race and living conditions, etc.

They are defined by the EPTRV (Expert Panel on Theory of Reference Values) and by the IFCC (International Federation of Clinical Chemistry and Laboratory Medicine) which have proposed a reference interval for each test, bounded by two limits, upper and lower, or by only one (value less than . . . or greater than . . . ), covering 95% of the population studied and considered healthy.

For each test, determination of its reference interval is a task that must meet international recommendations with regard to the following criteria:
determination of all the pre-analytical and physiological factors liable to interfere with the result,
establishment of the metrological characteristics of the measurement technique to be analysed,
collection and analysis of the specimens collected in this panel,
consequent determination of the reference interval, i.e. the area of normality included between the upper and lower bounds.

The question must therefore be asked as to whether there is a degree of normality for the measured values.

At a further stage, the question may even arise of assessing the meaning and relevance of variations within the range of normality. Is it possible to be more or less normal than normal? In other words, should a variation within this range of normality—which remains however within it—be taken into account or not? Should it be attributed any significance or not? It is not wrongful to question the relevance of variations within this buffer zone. This approach therefore makes it possible to go one step further in the analysis of evolution of biological tests by eliminating all references other than "normality" and "abnormality". In practical terms, what is not normal is abnormal and what is not abnormal is normal.

On the other hand, regarding the latter eventuality (abnormality), it is wise to take account of any relative variation from one examination to another in order to assess deterioration (increase in deviation) or improvement (reduction in deviation) of the situation. Various intuitive representations are possible aimed at simplicity and speed of reading. They form the basis for the present patent.

Account must be taken of the fact that different laboratories provide biological analysis results for the same individual.

Indeed, the same individual may frequently undergo examinations in several separate laboratories, independent from one another, outside his/her local laboratory, in so-called "community-based" outpatient medicine.

Thus, these biological data collected in private practice will be joined by data collected in the event that the patient's condition requires a stay in a hospital, which will call on its own laboratory.

This is also the case if a new physician, consulted by this patient in private practice, works with a different laboratory from that which the patient usually attends.

This is finally the case, throughout life, owing to a change of residence, during systematic health assessments (on joining an occupational, civil or military structure . . . ) or when an examination of this kind proves necessary, owing to a health problem when the individual is temporarily away from his/her usual place of residence.

Furthermore, it is a fact that advancing age leads to more frequent recourse to a greater number of practitioners, particularly on appearance of the signs of the aging process and/or with the onset of a chronic disorder. This situation often initiates recourse to one or several new privately practising specialists and subsequently a stay or stays in a hospital ward.

Finally, the individual may undergo examinations in other laboratories outside any context of disease at the time of marriage, recruitment, application for a loan, or a permit to practise a critical activity . . . , etc.

This is without counting all the "forgotten" or "unrecognised" examinations that have marked our existence since our birth. Examples particularly include contemporary biological tests to determine one's own blood group or systematic screening for signs of kidney weakness before any vaccination.

The question also arises of the consequences of making results available that originate from different laboratories.

As the price to pay for the ubiquity of biological tests performed in large numbers and by many different teams, the technical difficulties faced in consolidating the results are considerable and lie in benchmarks, practices and habits that are difficult to isolate.

The reference values and consequently the normal ranges can thus vary from one laboratory to another and within the same laboratory, when a change of equipment, consumable (reagent) or analysis method is adopted. Quite apart from these changes, regularly recalibrating the various tests—and thus possibly updating their values—is integral to good clinical biology practice and is part of accreditation procedures. The terms "normal range" or "range of normality", which have exactly the same meaning, will be used hereinafter.

Currently, in practice, one can measure the disparities encountered that appear already by consulting the results presented examination by examination, for the same patient, by two different laboratories. This operation will be performed by successively consulting the results provided on documents that are different and separate from each other.

This is because currently, the presenters of biological results available on the market in the form of spreadsheets allowing comparisons over time for one or more given tests are limited to displaying results from a single laboratory in the form of a comparative table, such as a spreadsheet, or in graphical form. As a general rule, this is the laboratory of the hospital in which the patient is hospitalised. In private practice, it is laboratory with whom the prescribing physician usually works, or the one chosen by the patient him/herself. In all cases, the data transmitted by the laboratory, whatever the latter is, are limited to its own production.

Whatever the case may be, this precludes an overall view allowing immediate comparative analysis on the same medium of the results of any individual who has had recourse to several laboratories (2 to N) and thus does not meet the needs of the various doctors and caregivers in charge of the patient.

PRIOR ART

For example, integration of all a patient's biological data is known through document U.S. Pat. No. 8,688,476. The aim of this invention is to ensure interoperability of biological data that are similar (a same test), but disparate (different in the way they are produced or expressed) and allow their presentation in a form structured over time in order to perform comparisons over time.

This representation allows any practitioner authorised by the patient to carry out exhaustive consultation of his/her collected biology results. This means that s/he will be able for the first time to read directly the results that his/her colleagues have prescribed to their common patient.

Strictly speaking, the curve that results from the combination of points corresponding to each measured value is artificial in that it combines heterogeneous elements that do not fit into the same ranges of normality.

Relevant reading of the represented data therefore implies an intellectual construction which consists in associating chronological reading of the successive points joined by a continuous line (despite their heterogeneity) with simultaneous reading of the vertical graphic element, located in the background for each measured value, indicating the interval within which this value is considered normal.

Such integration, for the same biological test, has a number of limitations however that can be summarised as follows:
  ethically, it can be criticised for plotting an "artificial" curve, since it does not link homogeneous points, which are at first sight comparable,
  intellectually, consultation of these data requires a form of gymnastics involving making a longitudinal transversal reading of this "value curve" at the same time as one needs to identify, point by point, the values which leave their own range of normality,
  the quantitative variations from one examination to another are difficult to assess, since two consecutive values do not have the same range of normality, several given examinations cannot be compared when they are not expressed in the same logic of units, either molar or weight or other, if this chronological representation of values is still possible, it is difficult to extrapolate a useful trend curve to assess the progression, stabilisation or regression of a chronic condition or acute episode.

This results in constraints related to the difficult reading of measured values, which lose much of their meaning due the fact that they are to be related, for each of the values, to different normal ranges.

DISCLOSURE OF THE INVENTION

The object of the present invention therefore aims to overcome the drawbacks of the prior art by proposing a new method of processing data obtained from biological analyses in order to facilitate utilisation of said data.

Another object of the present invention aims to offer healthcare personnel, by means of a new presentation of the results of biological analyses, another means of ensuring biological monitoring of the patient through consistent follow-up over time.

The objects assigned to the invention are achieved by means of a method for processing initial measured values $A(n)$ corresponding to results of biological analyses of the same patient from one or more laboratories, said analyses each relating to the same biological parameter, the method consisting in:

a) using for each initial value $A(n)$, measured and expressed by a given laboratory according to a unit of measurement proposed by said laboratory and a normal range ($BI(n)$, $BS(n)$), provided by the same laboratory, materialised by a range delimited between a lower bound $BI(n)$ and an upper bound $BS(n)$, or by a range lower than the upper bound $BS(n)$ only, or by a range higher than the lower bound $BI(n)$ only, b) recording data, encrypted or not, sent by a messaging system, advantageously secure, for their consolidation on a server, advantageously secure, according to a format determined based on heterogeneous presentations specific to each of these laboratories, wherein this format comprises, in addition to the measured value $A(n)$, metadata attached to it indicating the corresponding normal range and, opportunely, a certain number of data relating in particular to the corresponding laboratory, specifically to the conditions for carrying out the examination and/or analysis and indications on the identity of the patient and/or that of the prescriber, characterised in that it consists in:

c) using a mathematical model, with or without the aid of computer processing, to transform each of the initial values $A(n)$ obtained from each laboratory into a normalised value $Anorm(n)$, wherein a single laboratory is capable of providing several initial values $A(n)$ over time for the same patient, d) associating with all these normalised values $Anorm(n)$, the homogenised common normal range ($BInorm$, $BSnorm$) determined and retained for this homogenisation process, wherein said range is defined by a common simple homogenised lower bound $BInorm$ or by a common simple homogenised upper bound $BSnorm$ or, more frequently, by a common homogenised upper bound $BSnorm$ associated with a common homogenised lower bound, $BInorm$, with the knowledge that the normal ranges ($BI(n)$,$BS(n)$) provided by the same laboratory may vary over time, e) subsequently proposing, by means of any method of chronological or synthetic graphic representation appropriate to the use and/or to the user and/or to the data medium, a display comprising the successive different normalised values $Anorm(n)$ for the given biological parameter in combination with at least one element of data, visible, permanent or ephemeral, but always accessible, relating to the common homogenised normalised normal range ($BInorm$,$BSnorm$), determined and adopted for the homogenisation process, which forms the basis of the invention.

According to an embodiment in accordance with the invention, the method consists in using under a) for each value $A(n)$, measured by the laboratory having performed the biological analysis, the normal range ($BI(n)$,$BS(n)$) provided by this same laboratory.

According to an embodiment in accordance with the invention, the method consists in reading and recording for each value $A(n)$, the corresponding normal range ($BI(n)$,$BS(n)$) provided by the laboratory having performed the analysis and recording additional elements of data specific to the laboratory having performed the analysis, which relate in particular to the method of analysis used by this laboratory, the equipment employed and the reagents associated with the latter. Determination of this normal range, related to each biological test analysed, under defined conditions, is generally based on a sample representative of a population considered normal, according to a methodology specific to the laboratory or complying with a protocol defined by an accreditation body.

According to an embodiment consistent with the invention, the method consists in defining the "normalised" normal range for the initial value $A(n)$, by choice or calculation, represented either by a common normalised lower bound of normality $BInorm$, or by a common normalised upper bound of normality $BSnorm$, or more commonly, by combination of a common normalised lower bound of normality $BInorm$ and a common normalised upper bound of normality $BSnorm$.

According to an embodiment consistent with the invention, the transformation under (c) consists in calculating or determining, by means of a calculation based on linear correlations, the normalised value $Anorm(n)$ for each corresponding initial value $A(n)$.

According to an embodiment consistent with the invention, the method consists in, as part of determining the normalised values $Anorm(n)$, calculating a linear correlation coefficient $Cbs(n)$ based on the upper bound of normality $BS(n)$ and the initial value $A(n)$ and the difference between the upper bound $BS(n)$ and the lower bound $BI(n)$, with the knowledge that it is also possible to calculate the linear correlation coefficient $Cbi(n)$ based on the lower bound of normality $BI(n)$ and on the initial value $A(n)$ and the difference $BS(n)-BI(n)$ and that either coefficient $Cbs(n)$ or $Cbi(n)$ may be used interchangeably for the subsequent operations.

According to an embodiment consistent with the invention, the method consists in performing calculation of the linear correlation coefficient for each initial value $A(n)$ using the following equation:

$$Cbs(n)=(A(n)-BS(n))/(BS(n)-BI(n))$$

or $$Cbi(n)=(A(n)-BI(n))/(BS(n)-BI(n))$$

where BI(n) and BS(n) are respectively the lower and upper bounds of normality of the normal range in relation to the initial value A(n).

According to an embodiment consistent with the invention, the method consists in calculating the normalised values Anorm(n) using the following equation:

$$A\text{norm}(n) = B\text{Snorm} + Cbs(n) \times (B\text{Snorm} - B\text{Inorm})$$

or $$A\text{norm}(n) = B\text{Inorm} + Cbi(n) \times (B\text{Snorm} - B\text{Inorm})$$

where BInorm and/or BSnorm are respectively the common lower and/or upper bounds of normality of the common normalised normal range.

According to another embodiment, the method according to the invention consists in calculating, when the bound of normality BS(n) is infinite, a linear correlation coefficient Cb0(n) based on the lower bound of normality BI(n) and the initial value A(n) and on the difference between the lower bound BI(n) and the origin 0, by calculating the linear correlation coefficient for each initial value A(n), using the equation:

$$Cb0(n) = (A(n) - 0)/(BI(n) - 0)$$

where BI(n) is the lower bound of normality in relation to the initial value A(n), with BS(n) being an infinite value.

The method according to the invention subsequently consists in calculating the normalised values Anorm(n) using the following equation:

$$A\text{norm}(n) = B\text{Inorm} + Cb0(n) \times (B\text{Inorm} - 0)$$

where BInorm is the common normalised lower bound of normality of the common normalised normal range.

According to an embodiment consistent with the invention, the method consists in determining the common normalised upper bound of normality BSnorm and/or the common normalised lower bound of normality BInorm by arbitrary selection of their values. Preferentially and non-restrictively, the bounds BSnorm and BInorm are for example set respectively at 75 and 25 on a scale of between 0 and 100.

According to an embodiment consistent with the invention, the method consists in selecting from among the upper bounds of normality BS(n), the one having the highest value among all the BS(n) communicated by the different laboratories for the same measured biological test and/or from among the lower bounds of normality BI(n), the one having the lowest value among all the BI(n) in order to determine respectively the normalised upper bound of normality BSnorm and the normalised lower bound of normality BInorm.

According to an embodiment consistent with the invention, the method consists in determining the common normalised normal range (BInorm,BSnorm) by calculating the arithmetic mean over the values of all the normal ranges (BI(n),BS(n)) communicated by the different laboratories for the same measured biological test, without taking into account the respective positioning of the different BI(n) and BS(n) but only the intervals between the latter.

According to an embodiment consistent with the invention, the method consists in determining the common normalised upper bound of normality BSnorm by calculating the arithmetic mean of all the values of the upper bounds of normality BS(n) followed by that of the common normalised lower bound of normality BInorm by taking as the basis all the values of the lower bounds of normality BI(n), wherein the operation may also be performed by taking as the basis a limited number of these selectively chosen bounds BI(n) and/or BS(n).

According to an embodiment consistent with the invention, the method consists in, when at least one value A(n) is associated with a normal range having only a lower bound of normality BI(n), BS(n) being an infinite value, e1) on the one hand, when the value of A(n) is less than or equal to the value of BI(n), calculating a linear correlation coefficient Cb0(n) based on the lower bound of normality BI(n) and the initial value A(n) and on the difference between the lower bound of normality BI(n) and the origin 0, by calculating the linear correlation coefficient for each initial value A(n), using the equation:

$$Cb0(n) = (A(n) - 0)/(BI(n) - 0)$$

and calculating the normalised values Anorm(n), using the following equation:

$$A\text{norm}(n) = B\text{Inorm} + (Cb0(n) \times (B\text{Inorm} - 0))$$

e2) and on the other hand, when the value A(n) is greater than or equal to the value of BI(n), calculating the normalised value Anorm(n) using a mathematical equation verifying the condition that if the value of A(n) is between BI(n) and infinity, then Anorm(n) will be less than or equal to the value adopted for the normalised upper bound of normality BSnorm, thereby associating all the values Anorm(n) with a common normalised normal range (BInorm, BSnorm).

According to an embodiment consistent with the invention, the normalised value Anorm(n) is calculated using the following equation:

$$A\text{norm}(n) = B\text{Snorm} - ((B\text{Snorm} - B\text{Inorm})^2/(A(n) + B\text{Snorm} - B\text{Inorm} - BI(n)))$$

The common normalised bounds of normality, lower BInorm and upper BSnorm, are by way of example determined arbitrarily.

According to another embodiment, the method of the invention consists in, when at least one value A(n) is greater than or equal to its associated bound of normality BS(n):

calculating the linear correlation coefficient for each initial value A(n), using the following equation:

$$Cbs(n) = (A(n) - BS(n))/(BS(n) - BI(n))$$

or $$Cbi(n) = (A(n) - BI(n))/(BS(n) - BI(n))$$

and subsequently calculating for said value A(n) greater than or equal to its associated bound of normality BS(n), the normalised value Anorm(n), using the following equation:

$$A\text{norm}(n) = B\text{Snorm} + Ln(Cbs(n) \times (B\text{Snorm} - B\text{Inorm}))$$

or $$A\text{norm}(n) = B\text{Inorm} + Ln(Cbi(n) \times (B\text{Snorm} - B\text{Inorm}))$$

where BInorm and/or BSnorm are respectively the common lower and/or upper bounds of normality of the common normalised normal range.

According to another embodiment, the method of the invention consists in, when at least one value A(n) is less than or equal to its associated bound of normality BI(n):

calculating the linear correlation coefficient for each initial value A(n), using the following equation:

$$Cbs(n) = (A(n) - BS(n))/(BS(n) - BI(n))$$

or $$Cbi(n) = (A(n) - BI(n))/(BS(n) - BI(n))$$

and subsequently calculating for said value A(n) less than or equal to its associated bound of normality BI(n), the normalised value Anorm(n), using the following equation:

$$Anorm(n)=BSnorm-Ln(-Cbs(n)\times(BSnorm-BInorm))$$

or $$Anorm(n)=BInorm-Ln(-Cbi(n)\times(BSnorm-BInorm))$$

where BInorm and/or BSnorm are respectively the common lower and/or upper bounds of normality of the common normalised normal range.

The "Ln" function shown above corresponds to the Napierian logarithm function. This function can be replaced, without going beyond the ambit of the present invention, by the "Log" function corresponding to the decimal logarithm function. The above equations are therefore not repeated for this purpose.

Furthermore, in addition to the two preceding paragraphs, the method according to the invention consists in, when a value A(n) is on the one hand less than or equal to its associated bound of normality BS(n) and on the other hand greater than or equal to its associated bound of normality BI(n):

calculating the linear correlation coefficient for each initial value A(n), using the following equation:

$$Cbs(n)=(A(n)-BS(n))/(BS(n)-BI(n))$$

or $$Cbi(n)=(A(n)-BI(n))/(BS(n)-BI(n))$$

and subsequently calculating for said value A(n) less than or equal to its associated bound of normality BS(n) and greater than or equal to its associated bound of normality BI(n), the normalised value Anorm(n), using the following equation:

$$Anorm(n)=BSnorm+Cbs(n)\times(BSnorm-BInorm)$$

or $$Anorm(n)=BInorm+Cbi(n)\times(BSnorm-BInorm)$$

where BInorm and/or BSnorm are respectively the common lower and/or upper bounds of normality of the common normalised normal range.

According to an embodiment consistent with the invention, the method allows use of all the raw initial values A(n), without prior processing or transformation and moreover independently of the fact that these values A(n) are each defined by a finite range of normality (between BS(n) and BI(n)) or simply in relation to a single lower bound BI(n) or upper bound BS(n), without any detriment to the homogeneity of the values Anorm(n) thus obtained.

According to an embodiment consistent with the invention, the method allows use of all the raw initial values A(n), without prior processing or transformation and moreover independently of the unit of measurement in which each of the initial values A(n) is expressed, which has the effect, for example non-restrictively, of rigorously amalgamating results expressed in a volume logic (molar) or weight logic (grams and multiples or sub-multiples).

According to an embodiment consistent with the invention, the method consists in displaying a graph on which the corresponding dates and results of the analyses (n) for the same test and the same patient are plotted along a horizontal axis, in chronological order, and on the other hand, along a vertical axis, for all these analyses, the single common normalised normality range (BInorm, Bsnorm) associated with normalised values Anorm(n), the positions of the different neighbouring normalised values Anorm(n) being connected by line segments ranging from one normalised value Anorm(n) to the next Anorm (n+1), while the single common normalised normality range (BInorm, Bsnorm) is represented in the form of a vertical rectangle or any other line or geometrical figure or materialisation representative of this "normalised" range of normality.

According to an embodiment consistent with the invention, the method consists in defining on the location area of each normalised value Anorm(n), an active area, which when pointed to or selected by means of a mouse or any other instrumental or digital action, makes it possible to display ephemerally a window containing at least some of the data forming the element of metadata corresponding to the measured value in question.

According to an embodiment consistent with the invention, the method consists in ensuring or reinforcing safeguarding of the data by using any intrinsic data encryption process or, extrinsically, during transfer or storage of data on location and during the processing phases and operations under the terms of the invention or during the subsequent stages of making available raw or processed data concerning the patient in question in order to maintain and ensure the integrity, confidentiality and security of such personal health data according to the best means available according to the state of the art.

According to an embodiment consistent with the invention, the method consists in importing additional medical data from a patient's personal electronic medical record (PEMR), such as start/end of medical treatment, health problem, stay in regions with a health risk or others, in order to complete the graphic representation at the request of health personnel, by combining—insofar as necessary—different types of medical data from either clinical diagnostic or imaging registers or therapeutic registers, in particular medicinal product registers, in order to create tables of "preferences" corresponding to the uses and needs of caregivers for optimal patient management.

According to an embodiment consistent with the invention, the method allows, for a given biological test or for a selected set of tests and/or for concatenation with data other than biological data as described in claim 20, consolidation of corresponding comparable data between a number of patients in order to create a silo of massive data previously rendered completely and definitively anonymous without possible backtracking to individual identities, for the purpose of scientific, industrial or public health studies independently of the initial technical degree of heterogeneity of the data thus taken into account.

According to one embodiment, the method of the invention consists in importing additional medical data from a patient's personal electronic medical record (PEMR), such as start/end of medical treatment, health problem, stay in regions with a health risk or others, in order to complete the graphic representation at the request of health personnel. These associations, the list of which is non-exhaustive, are intended to facilitate monitoring and management of a treatment, by adapting doses for example, or to generate alerts or reminders.

The method according to the invention therefore offers the remarkable advantage of employing a relevant graphic construction allowing immediate comparability of the measured values for which their associated range of normality may be different.

Several major advantages resulting from the method according to the invention should be mentioned, namely:
- it becomes easy to compare a given examination or examinations carried out in different laboratories,
- it becomes easy for each practitioner caring for the patient to consult all the biological data of his/her patient, including those requested by his/her colleagues, whether known or unknown,
- graphic representation of the values within identical ranges of normality allows easy and immediate observation of a highly significant evolutionary curve in order to assess the stabilisation, progression or regression of a chronic disorder or an acute episode,
- this representation makes it possible to monitor the onset and appearance of a disorder by observing the evolution of specific markers performed in several laboratories,
- there is no need to multiply the examination codes according to the LOINC® or other classification (SNOMED, X12 etc.,); the semantic reconciliation process can be performed based on different computer codes, at a later date on a dedicated server,
- the measured value rates can be expressed on a single graph, even if they are expressed based on analytical samples with different volumes,
- It even becomes possible to precisely and accurately compare test results, the values of which are expressed in different units, for example, in moles or grams,
- homogenisation of all these values allows their relevant integration in a massive data thesaurus (Big Data), by eliminating the heterogeneity of the data acquired in totally independent series, within the framework of public health data,
- other advantages will become apparent, particularly for selection and management of the participants in clinical trials, completely transforming the logic of the inclusion or withdrawal processes,
- hence, reading an individual's longitudinal biological record, a thesaurus of all the examinations carried out during his/her life, will give full meaning to the theoretical predispositions displayed by genomic data or by tissue groups.

BRIEF DESCRIPTION OF THE DRAWINGS

Other characteristics and advantages of the present invention will appear more clearly upon reading the following description made with reference to the appended drawings given as non-limiting examples wherein:

FIGS. 1a and 1b are examples of conventional, unstructured presentation of biological analysis results, wherein each of the two examples is to be considered as an image, with no possibility of processing the data.

FIGS. 3a and 3b are examples of metadata appearing ephemerally when the area or box in question is prompted and containing the data of the measured value, said metadata being visible in the projection of the presentation of the structured biological results, either in the form of a spreadsheet (FIG. 3a) or a graph (FIG. 3b), FIG. 4 illustrates with a flowchart three main stages of the method of the invention relating to homogenisation according to the invention of the normal ranges, namely (in stage 1) calculation of the linear correlation coefficient, (in stage 2) the choice of the upper and lower normalised bounds of normality and subsequently calculation of the measured value transposed into this new normality environment and finally (in stage 3) graphical representation of these normalised or homogenised data.

EMBODIMENT(S) OF THE INVENTION

Structurally and functionally identical elements present on several separate figures are assigned the same numerical or alphanumerical reference.

FIGS. 1a and 1b are examples of conventional, unstructured presentation of biological analysis results. Differences in normal ranges are observed for example (0.17-0.43 in FIG. 1a versus 0.20-0.50 in FIG. 1b), for urea for example, which make immediate consolidation in a structured mode impossible for the same patient, the same test and the same choice of units.

Figure 2A:
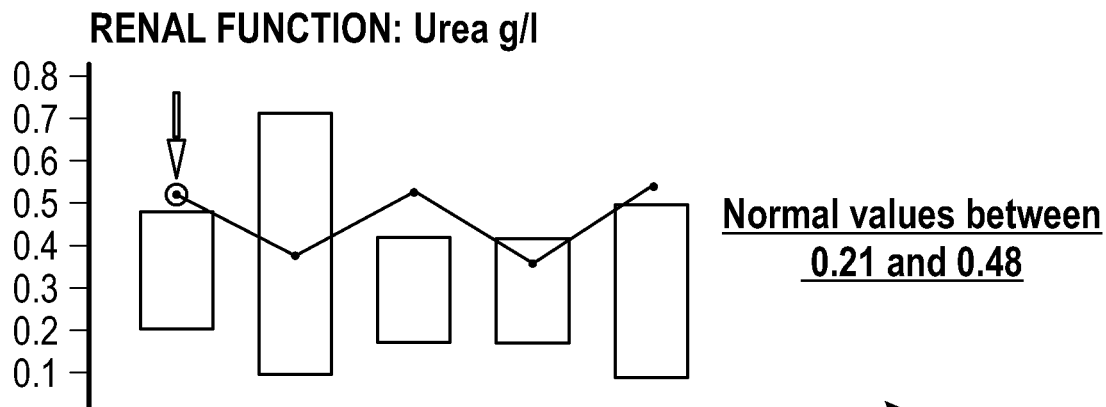
FIGS. 2a, 2b and 2c are examples of structured presentation of biological results without normalisation of the associated normal ranges, with a first degree of comparability of said results.
Figure 2B:
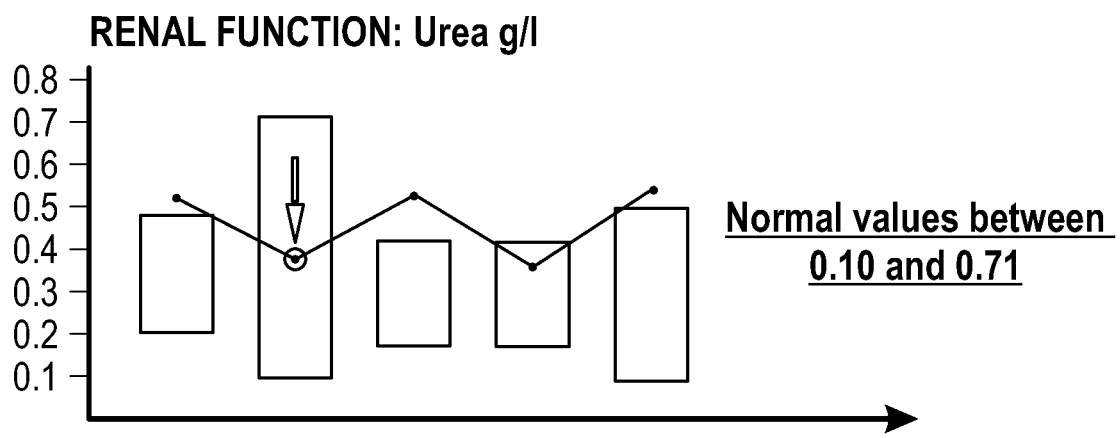
Figure 2C:
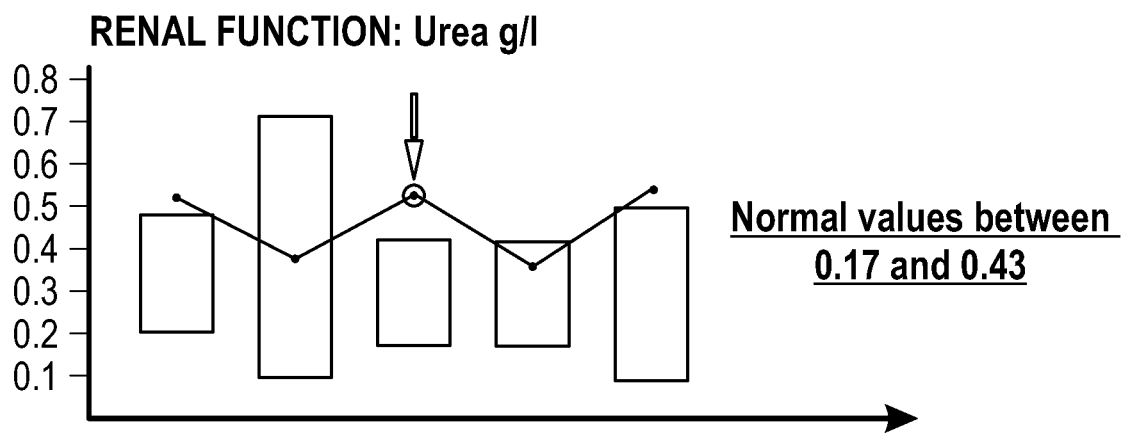

FIGS. 2a, 2b and 2c are examples of structured presentation of biological results without normalisation of the associated normal ranges in the prior art.

Hence, it is already an advancement to be able to represent in a structured manner, as on the three following graphs (FIGS. 2a, 2b, 2c), the values measured during chronologically successive tests on the same patient while allowing consultation "on the fly" of the corresponding range of normality for each measured value.

It is thus possible to solve the technical problems of all kinds that prevented this consolidation. Among these:
the title of the test (it should be remembered that fifteen different names exist in French denoting a "red corpuscle" and not fewer than nine in English,
the volume of the sample (mm3, dL and L are the most common),
the ranges of normality that are often different from one laboratory to another,
the units used (weight logic or molar logic),
computer encoding (multiple versions of HL7 or HPrim standards etc. . . . ),
without forgetting the wide array of patient identifiers in the different structures.

It is therefore possible to obtain a relevant consolidated representation, on the same spreadsheet or on the same graph, as for example in FIGS. 3a and 3b which are examples of ephemeral metadata, in projection of the presentation of structured biological results, in the form of a spreadsheet (FIG. 3a) and a graph (FIG. 3b) in the prior art.

This consolidation is obtained by aggregating these results, after eliminating successive levels of incompatibilities, without touching the native data and by showing in the form of ephemeral metadata—by a line in a spreadsheet (FIG. 3a) or by a representative geometric figure (FIG. 3b)—the range of normality for the measured value in question.

In FIG. 3a, the ephemeral metadata appear by pointing to the box identified by the * sign, containing the measured value "8.68" dated 26 May 2014 and the corresponding range of normality.

In FIG. 3b, the ephemeral metadata appear by pointing to the black circle (which is then immediately surrounded by a grey halo) indicating the measured value. The values, low (2.84) and high (7.18), of the range of normality can be permanently viewed using the vertical rectangle on which the measured value "8.68" is positioned.

FIG. 4 illustrates with a flowchart three main stages of a method of the invention relating to homogenisation of the normality intervals.

The first part consists in, for each value A(1), A(2) . . . A(n), n similar measured values (to be compared) resulting from a same biological test performed on successive dates for a given patient, calculating the respective linear correlation coefficients Cbs(1), Cbs(2) . . . Cbs(n) (stage 1a) between these values A(1), A(2) . . . A(n) and the values BS(1), BS(2) . . . BS(n), for n values provided by the biological analysis laboratories, representing the upper bound of normality BS(n) respectively for each value A(n). The whole number n corresponds to a date.

An alternative embodiment of the method according to the invention, non-exclusive of the previous embodiment, will be to rely on calculation of the respective linear correlation coefficients Cbi(1), Cbi(2) . . . Cbi(n) (stage 1b) between these same measured values A(1), A(2) . . . A(n) and the values BI(1), BI(2) . . . BI(n), for n provided by the biological analysis laboratories, respectively representing for each value A(n) the lower bound of normality BI(n).

Hence, the values Cbs(1), Cbs(2), . . . Cbs(n) for each value A(1), A(2), . . . , A(n), are obtained by the following relationship:

$$Cbs(n)=(A(n)-BS(n))/(BS(n)-BI(n)).$$

Likewise, the values Cbi(1), Cbi(2), . . . Cbi(n) for each value A(1), A(2) . . . , A(n) are obtained by the following relationship:

$$Cbi(n)=(A(n)-BI(n))/(BS(n)-BI(n)).$$

In general:
the value of BS(1) is different from or equal to the value of BS(2) which is different from or equal to the value of BS(n) etc. . . .
the value of BI(1) is different from or equal to the value of BI(2) which is different from or equal to the value of BI(n) etc. . . .
the difference between the value of BS(n) and the value of BI(n) is greater than zero,
the values of BS(n) and BI(n) are greater than or equal to zero,
the value of "n" belongs to the range of integers.

The second part of the method according to the invention consists in defining a common normalised range of normality for each value A(n).

This is obtained by selecting (stage 2a):
an identical value for the normalised upper bound of normality, BSnorm, for all the values BS(1), BS(2) . . . BS(n) etc. . . . . . Thus, whatever the value of n, the BSnorm(n) values are equal to BSnorm.
another identical value for the normalised lower bound of normality, BInorm, for all the values BI(1), BI(2) . . . BI(n) etc. . . . . . Thus, whatever the value of n, the BInorm(n) values are equal to BInorm.

Thus, the new normalised values of A(1), A(2) . . . A(n) denoted respectively Anorm(1), Anorm(2) . . . Anorm(n) are obtained by the following relationship (stage 2c):

$$Anorm(n)=BSnorm+(Cbs(n)\times(BSnorm-BInorm)).$$

Alternatively, according to the variant formalised in the first part of this method, the new values, denoted normalised values, Anorm(1), Anorm(2) ... Anorm(n) are likewise obtained by the following relationship (stage 2b):

$$Anorm(n)=BInorm+(Cbi(n)\times(BSnorm-BInorm)).$$

Each normalised value Anorm(n) can therefore be positioned within its normalised normal range or in relation to said normalised normal range.

The third part of the method according to the invention consists in representing the values thus defined in graph form.

In order to do this, a diagram (orthogonal or not) can be taken as the basis, having for example:
- on the ordinate, the scale of the values that can be adopted by all the values Anorm(1), Anorm(2) ... Anorm(n), the values BSnorm(1), BSnorm(2) ... BSnorm(n) and the values BInorm(1), BInorm(2) ... BInorm(n)
- and having, on the abscissa, the dates "t", classified in chronological order, on which the results A(1) were produced on the date "t1", A(2) on the date "t2" ... A(n) on the date "tn", The values Anorm(1), Anorm(2) ... Anorm(n), the values BSnorm(1), BSnorm(2) ... BSnorm(n) and the values BInorm(1), BInorm(2) ... BInorm(n) are represented graphically by a dot, or by any other symbol, according to their respective date t1, t2 ... tn.

Figure 5:
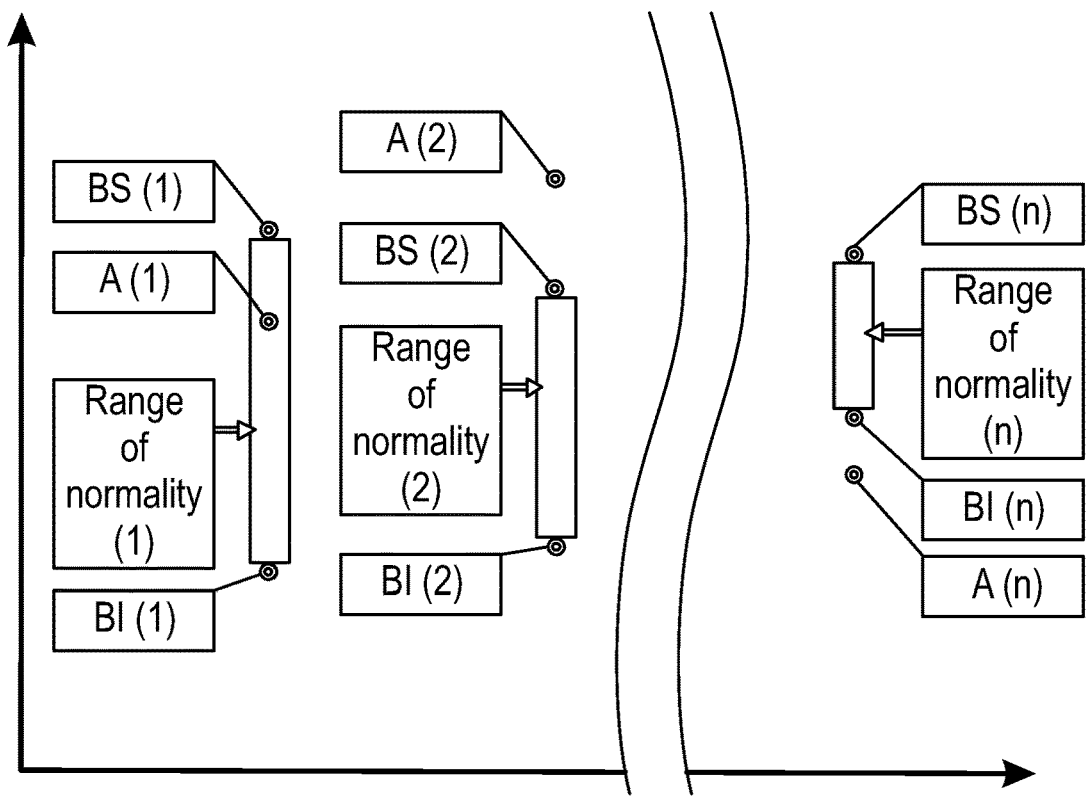
FIG. 5 illustrates the graphic result, within the context of application of the method according to the invention, of a series of measured values A(n), associated with their respective normal ranges materialised by the upper BS(n) and lower BI(n) bounds.

FIG. 5 illustrates the graphic result of a sequence of measured values A(n), associated with their respective normal ranges materialised by the upper BS(n) and lower BI(n) bounds, The initial values A(1), A(2), ..., A(n) were thus measured on different dates and namely by identical or different laboratories.

Figure 6:
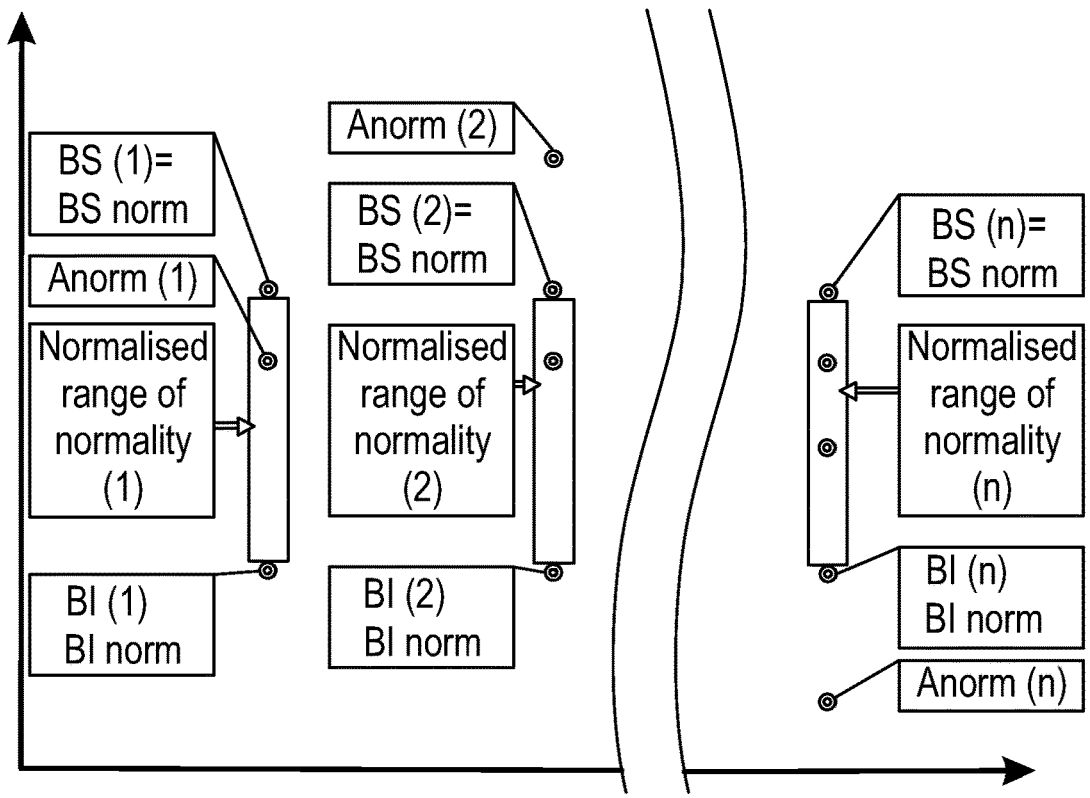
FIG. 6 illustrates the graphic result of application of the method according to the invention to a sequence of measured values A(n) of FIG. 5, transformed into normalised measured values Anorm(n), associated with their respective normalised normal ranges, materialised by the common normalised upper bound BSnorm and the common normalised lower bound BInorm.

FIG. 6 illustrates the graphic result of application of a method according to the invention to a sequence of measured values A(n) transformed into normalised measured values Anorm(n), associated with their respective normalised range of normality. This common normalised normal range (also called range of normality above) is materialised by the upper and lower normalised bounds of normality BSnorm and BInorm.

Figure 7:
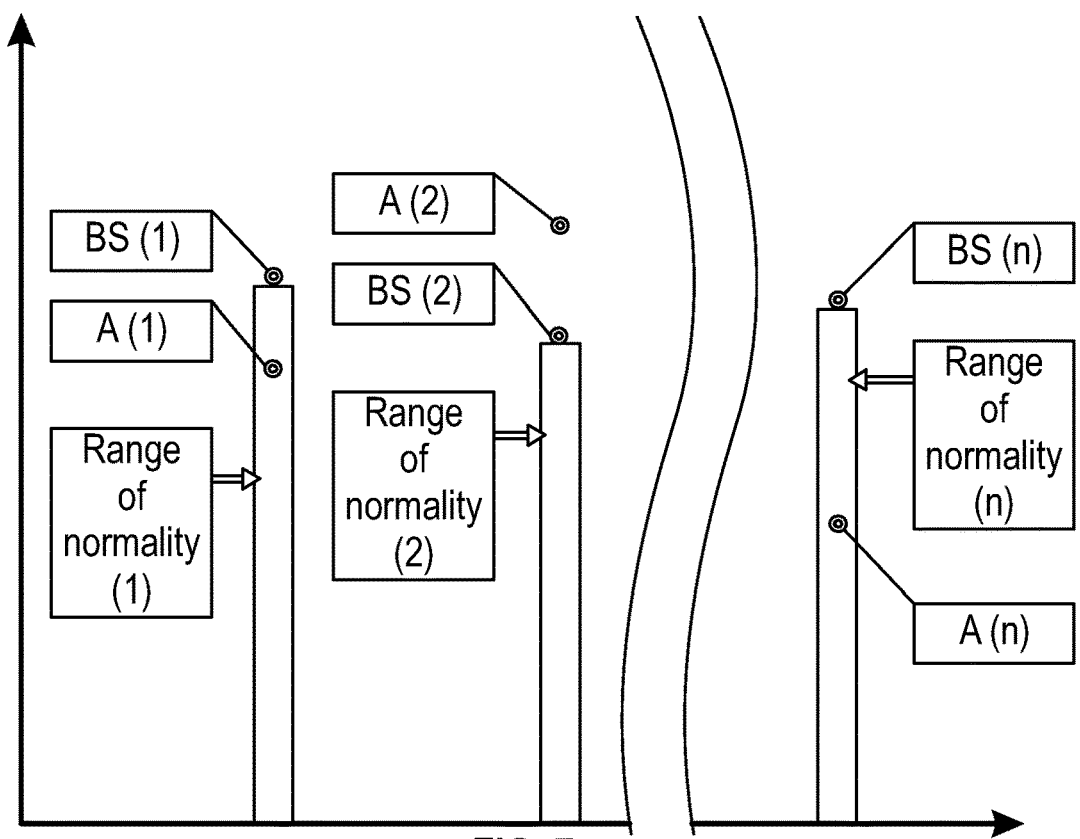
FIG. 7 illustrates the graphic result of a sequence of measured values A(n) associated with their respective normal ranges, materialised by respective upper bounds of normality BS(n) and intended to be processed as part of the method according to the invention.

FIG. 7 illustrates the graphic result of a sequence of measured values A(n), associated with their respective ranges of normality, materialised by respective upper bounds of normality BS(n).

Figure 8:
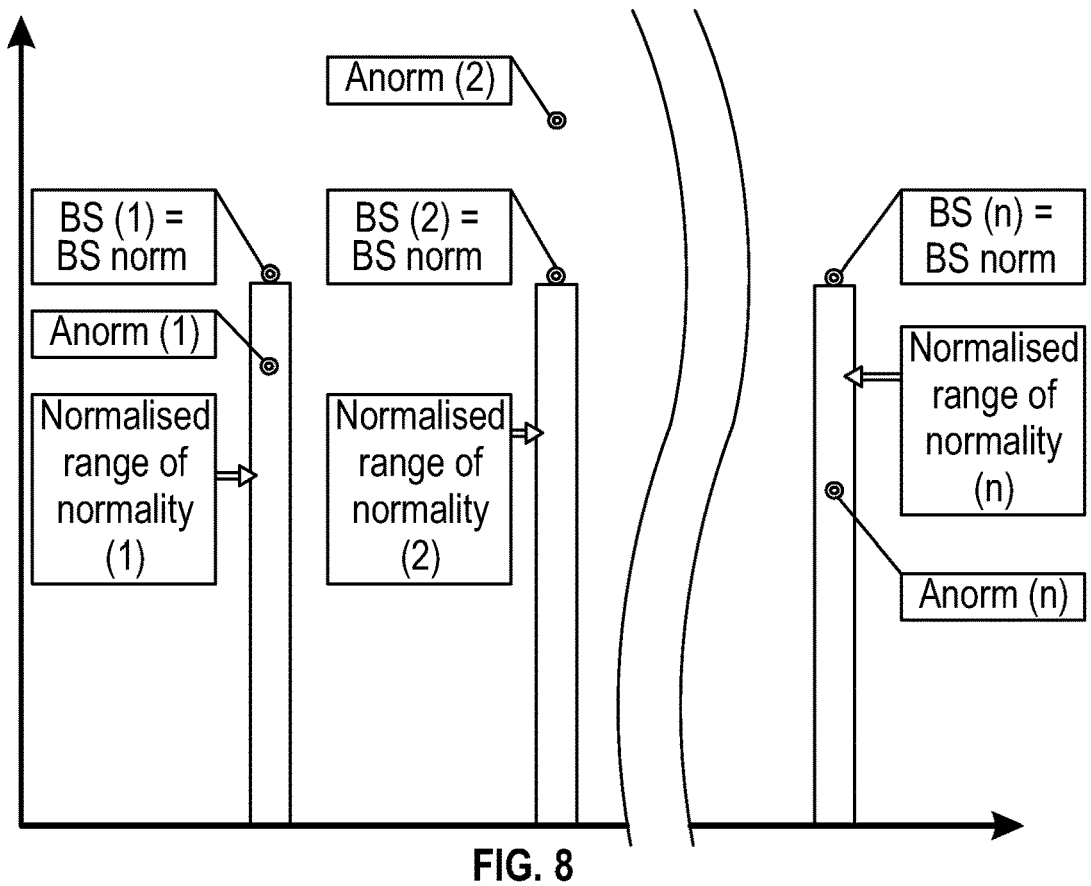
FIG. 8 illustrates the graphic result of application of the method according to the invention to a sequence of measured values A(n) in FIG. 7, transformed into normalised measured values Anorm(n), associated with their respective normalised normal ranges, materialised by the common normalised upper bound BSnorm.

FIG. 8 illustrates the graphic result of application of a method according to the invention to this sequence of measured values A(n) transformed into normalised measured values Anorm(n), associated with their respective common normalised normal ranges. The latter is materialised by normalised upper bounds of normality that all have the same value BSnorm.

Such an example corresponds to the case of homogenisation of results, when the biological analysis laboratories stipulate that the range of normality is "less than or equal to" or "strictly less than" an upper bound of normality BS(n).

The method according to the present invention is broken down into three parts described in detail below.

The first part consists in, for each value A(1), A(2) ... A(n), n similar values resulting from biological tests for a given patient, calculating the respective linear correlation coefficients Cbs(1), Cbs(2) ... Cbs(n) between these values A(1), A(2) ... A(n) and the values BS(1), BS(2) ... BS(n), wherein n values provided by the biological analysis laboratories represent the upper bound of normality respectively for each value A(n).

A variant for the first part of this method consists in, for each value A(1), A(2) ... A(n), n similar values resulting from the biological tests for a given patient, calculating the respective linear correlation coefficients Cbi(1), Cbi(2) ... Cbi(n) between these values A(1), A(2) ... A(n) and the values BI(1), BI(2) ... BI(n), wherein n values provided by the biological analysis laboratories represent the lower bound of normality respectively for each value A(n).

Within the context of this specific case in which the range of normality of a value A(n) is "less than or equal to" or "strictly less than" a bound BS(n), the value 0 (zero) must be associated with the bound BI(n) for the n value(s) considered.

Hence, the values Cbs(1), Cbs(2), ... Cbs(n) for each value A(1), A(2), ... A(n), are obtained by the following relationship:

$$Cbs(n)=(A(n)-BS(n))/(BS(n)-0).$$

The values Cbi(1), Cbi(2), ... Cbi(n) for each value A(1), A(2), ... A(n) are obtained by the following relationship:

$$Cbi(n)=(A(n)-0)/(BS(n)-0).$$

In general:
- The value of BS(1) is different from or equal to the value of BS(2) which is different from or equal to the value of BS(n) etc. ...
- The difference between the value of BS(n) and the value of BI(n) is greater than zero,
- The values of BS(n) and BI(n) are greater than or equal to zero,
- The value of "n" belongs to the range of integers.

The second part of this method consists in normalizing the range of normality of each value A(n) by imposing:
- an identical value "BSnorm" on all the values BS(1), BS(2) ... BS(n) etc. ... and thus, whatever the value of n, the BS(n) values are equal to the BSnorm values,
- another identical value "BInorm" on all the values BI(1), BI(2) ... BI(n) etc. ... and thus, whatever the value of n, the BI(n) values are equal to the BInorm values.

Thus, the new normalised values of A(1), A(2) ... A(n) denoted respectively Anorm(1), Anorm(2) ... Anorm(n) are obtained by the following relationship:

$$Anorm(n)=BSnorm+(Cbs(n)\times(BSnorm-BInorm)).$$

Also according to the variant formalised in the first part of this method, the new values Anorm(1), Anorm(2) ... Anorm(n) are likewise obtained by the following relationship:

$$Anorm(n)=BInorm+(Cbi(n)\times(BSnorm-BInorm)).$$

The third part of this method consists in, on a frame of reference (orthogonal or not) having:
- on the ordinate the scale of the values that can be adopted by all the values Anorm(1), Anorm(2) ... Anorm(n), the values BSnorm(1), BSnorm(2) ... BSnorm(n) and the values BInorm(1), BInorm(2) ... BInorm(n)
- and having on the abscissa the dates "t", classified in chronological order, on which the results A(1) were produced on the date "t1", A(2) on the date "t2" ... A(n) on the date "tn", The values Anorm(1), Anorm(2) ... Anorm(n), the values BSnorm(1), BSnorm(2) ... BSnorm(n) and the values BInorm(1), BInorm(2) ... BInorm(n) are subsequently represented graphically by a dot, or any other symbol, according to their respective date t1, t2 ... tn.

Figure 9:
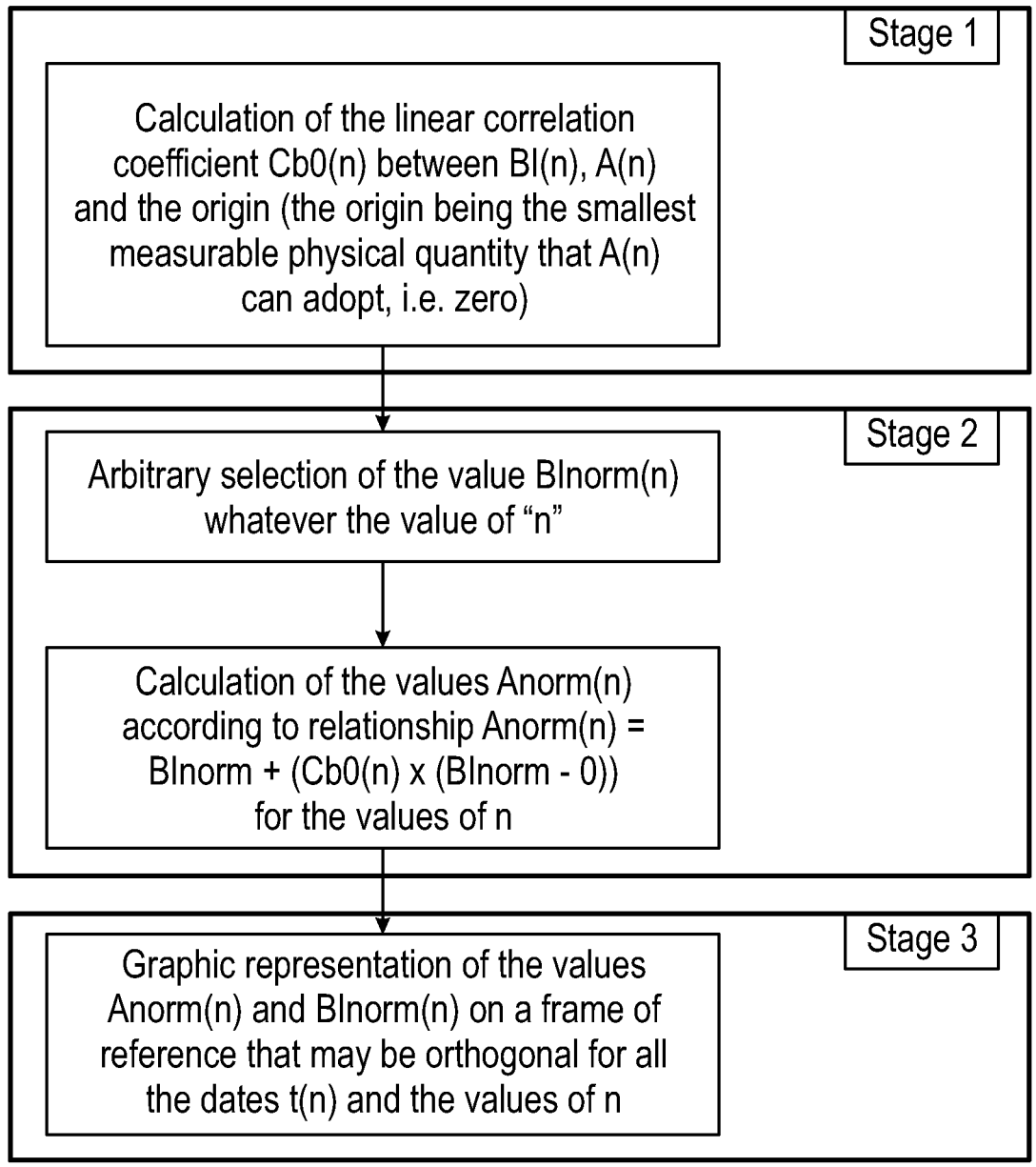
FIG. 9 illustrates with a flowchart three main stages of the method according to the invention within the context of a specific case in which the normal range associated with a measured value A(n) is greater than or equal to or strictly greater than a lower bound of normality BI(n)

FIG. 9 illustrates with a flowchart the three main stages of a method according to the invention within the context of a specific case in which the range of normality (or the normal range) of a measured value A(n) is greater than or equal or strictly greater than a lower bound of normality BI(n) and in the case in which all the values A(n) to be compared are associated with this same type of normal range (i.e. said normal ranges are defined as always and only greater than, or greater than or equal to, a lower bound of normality BI(n) for a given patient).

Figure 10:
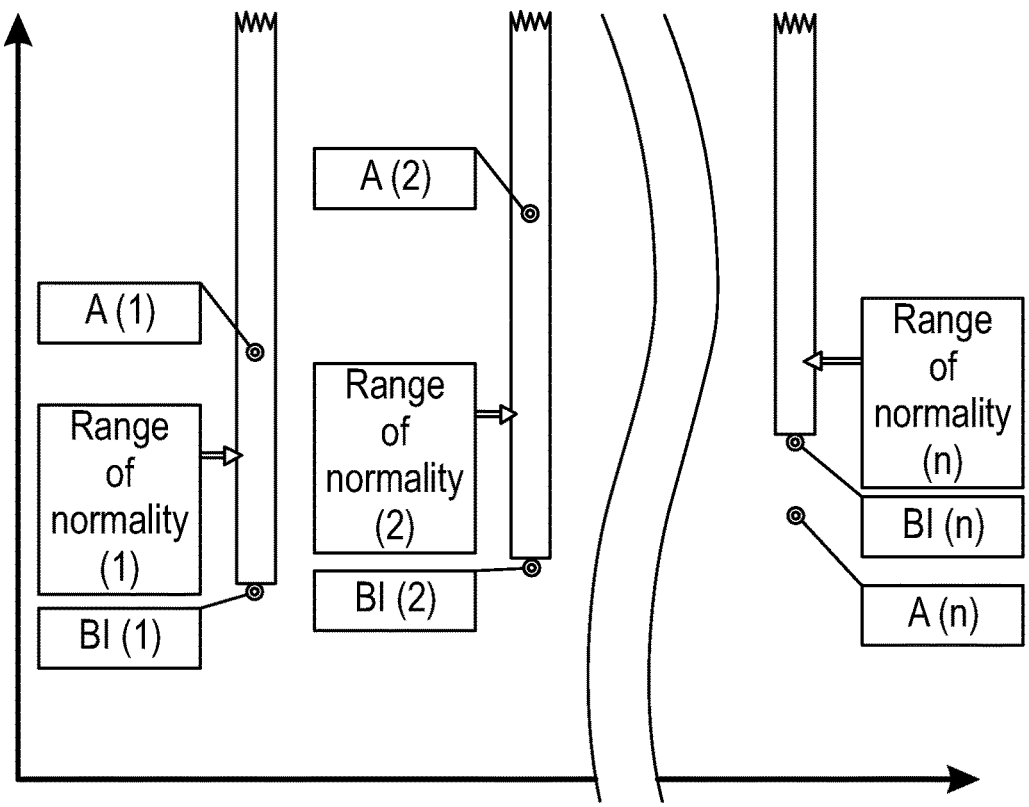
FIGS. 10 and 11 illustrate the graphic result of application of the method in FIG. 9 to a sequence of values A(n) associated with their respective normal ranges materialised by the lower bounds of normality BI(n), (FIG. 10) and the normalised lower bound of normality BInorm, (FIG. 11), wherein the upper bounds of normality BS(n) are equal to infinity.
Figure 11:
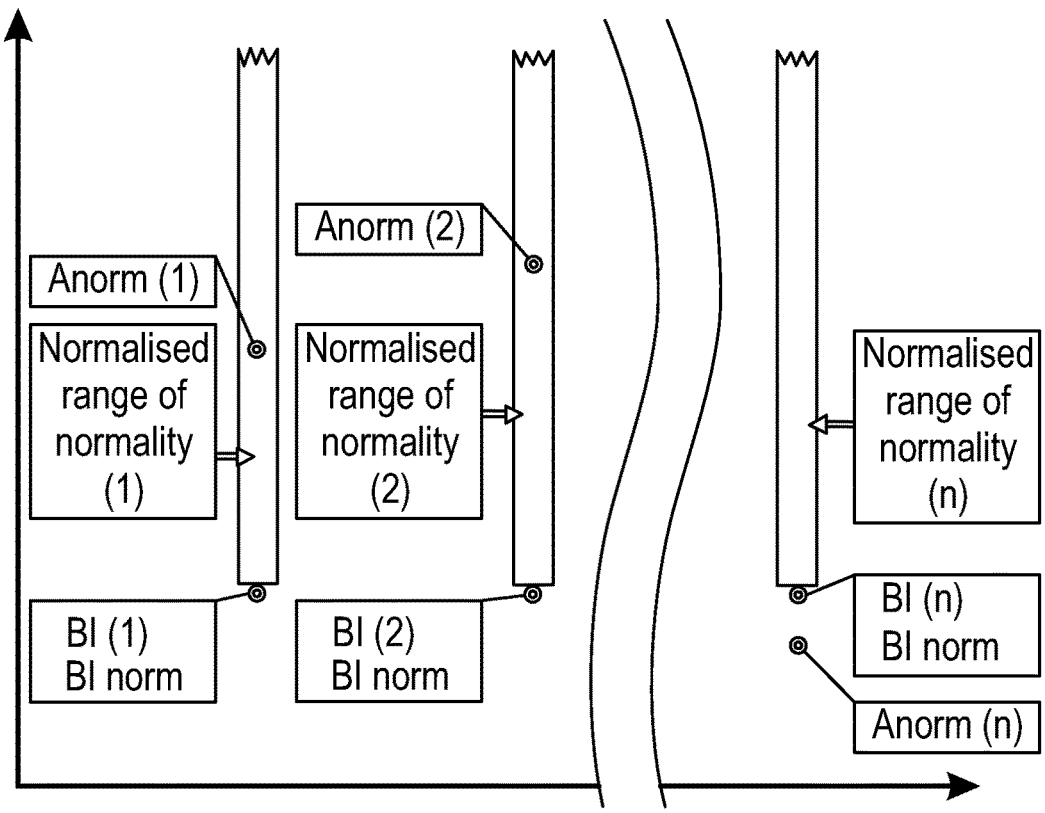

Within the context of this specific case illustrated in FIGS. 9, 10 and 11, the coefficients Cbs(n) and Cbi(n) are not calculable, as the upper bound of normality BS(n) is equal to infinity.

The method according to the present invention is thus broken down into three main parts described below.

The first part consists in, for each value A(1), A(2) . . . A(n), n similar values resulting from biological tests for a given patient, calculating the linear correlation coefficients Cb0(1), Cb0(2) . . . Cb0(n) between the values A(1), A(2) . . . A(n) and the values BI(1), BI(2) . . . BI(n), (n values provided by the biological analysis laboratories respectively representing for each value A(n) the lower bound of normality BI(n)) and the origin, i.e. zero (the smallest measurable physical quantity that A(n) can adopt).

It is then defined that the values Cb0(1), Cb0(2) . . . Cb0(n) for each value A(1), A(2) . . . A(n) are obtained by the following relationship:

$$Cb0(n)=(A(n)-0)/(BI(n)-0).$$

In general:
the value of BI(1) is different from or equal to the value of BI(2) which is different from or equal to the value of BI(n) etc. . . . ,
the difference between the value of BS(n) and the value of BI(n) is greater than zero,
the values of BS(n) and BI(n) are greater than or equal to zero,
the value of "n" belongs to the range of integers.

The second stage of this method consists in normalising the range of normality of each value A(n) by imposing:
an identical value "BInorm" on all the values BI(1), BI(2) . . . BI(n) etc. . . . and thus, whatever the value of n, the BI(n) values are equal to the BInorm values.

Thus, the new values Anorm(1), Anorm(2) . . . Anorm(n) are obtained by the following relationship:

$$Anorm(n)=BInorm+(Cb0(n)\times(BInorm-0)).$$

The third stage of this method consists in positioning the values Anorm(n) on a frame of reference (orthogonal or not) having:
on the ordinate the scale of the values that can be adopted by all the values Anorm(1), Anorm(2) . . . Anorm(n) and the values BInorm(1), BInorm(2) . . . BInorm(n)
and on the abscissa the dates "t", classified in chronological order, on which the results A(1) were produced on the date "t1", A(2) on the date "t2" . . . A(n) on the date "tn", The values Anorm(1), Anorm(2) . . . Anorm(n) and the values BInorm(1), BInorm(2) . . . BInorm(n) are represented graphically by a dot, or any other symbol, according to their respective date t1, t2 . . . tn.

Figure 12A:
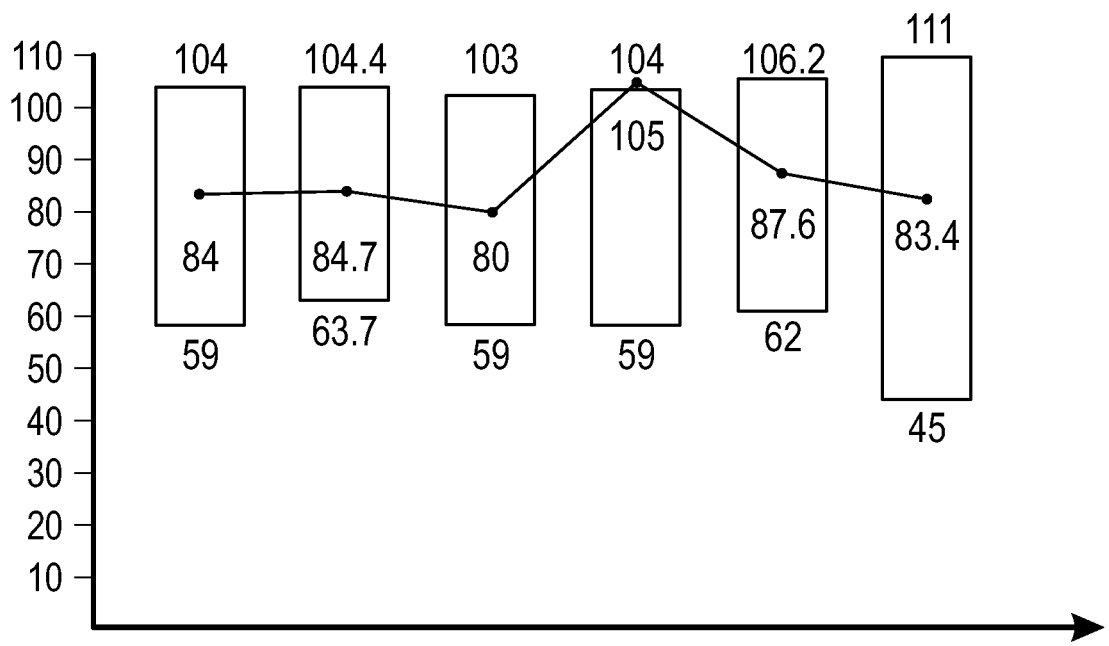
FIGS. 12a and 12b illustrate homogenisation of the ranges of normality within a panel of different laboratories, according to the method of the invention.
Figure 12B:
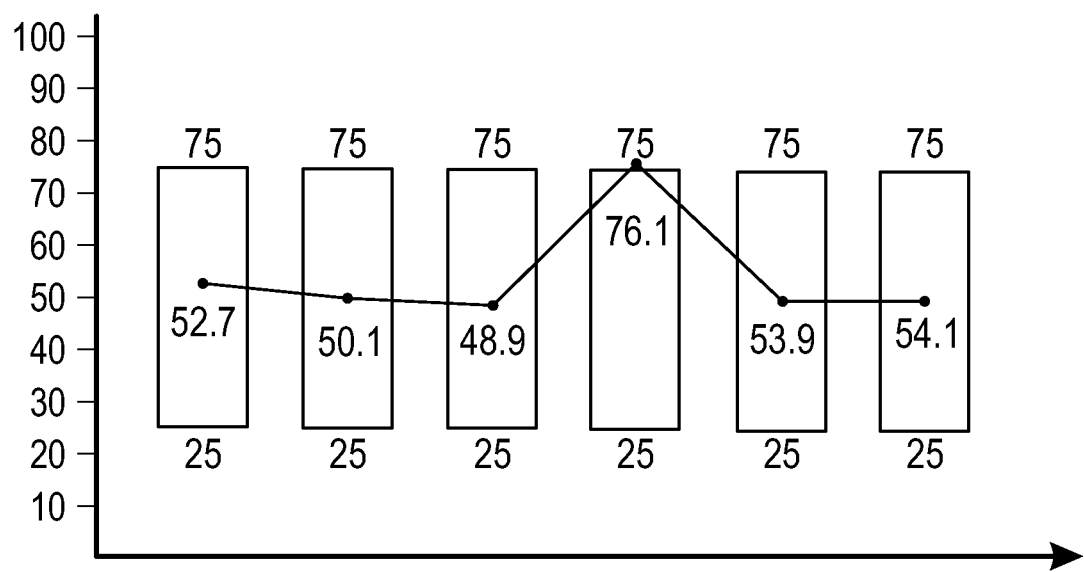

FIGS. 12a and 12b illustrate an example of homogenisation of the ranges of normality within a panel of different laboratories, according to a method of the invention.

In this example, illustrated in said FIGS. 12a and 12b, homogenisation is illustrated within a panel of different laboratories:
Blood creatinine level expressed in mmol/l
6 separate laboratories, 5 different ranges of normality In this example, six successive measurements of blood creatinine level are shown, i.e.:
84, 84.1, 80, 105, 87.6, 83.4

For ranges of normality (normal ranges, intervals) which are respectively:
59-104, 63.7-104.4, 59-103, 59-104, 62-106.2, 45-111

By calculation, we have arbitrarily selected a normality interval of 25-75, which is close to the mean of the sum of the represented intervals (the mean of the interval values being 49.2). Any scale can be selected, but it is relevant to remain close to this mean value for range of normality.

Hence, homogenised values no longer have any meaning of their own, but conversely, their evolutionary curve over time acquires its full meaning and corrects potentially erroneous visual perceptions. Thus:
the first discretely ascending curve segment (from 84 to 84.7 for the first two measured values) becomes descending after homogenisation, reflecting an inverse evolution (from 52.7 to 50.1),
conversely, the last segment, descending before any correction (from 87.6 to 83.4) actually becomes ascending (from 53.96 to 54.1).

Figure 13A:
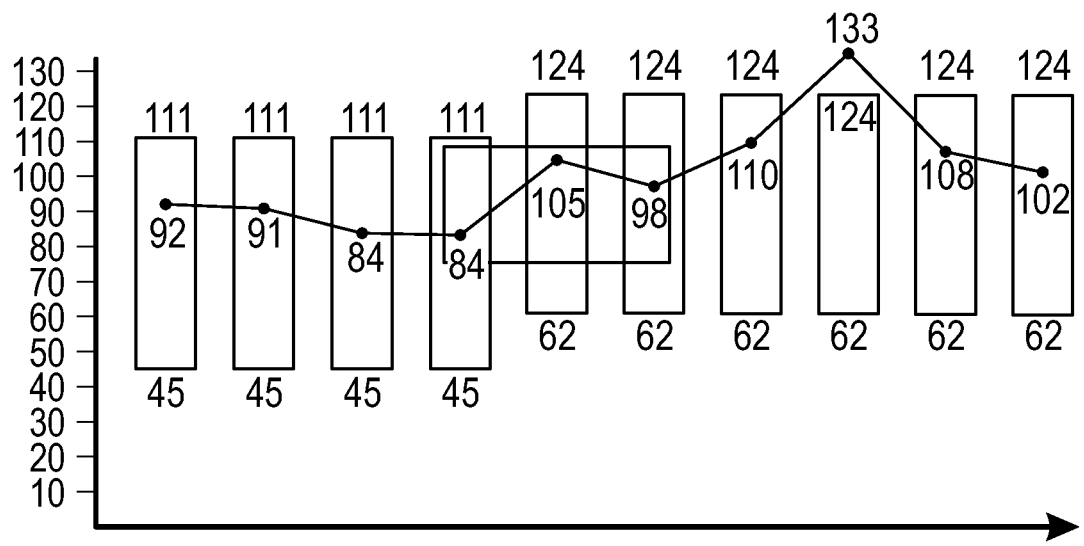
FIGS. 13a and 13b illustrate homogenisation of the ranges of normality within a same laboratory, owing to a change of examination procedure, according to the method of the invention.
Figure 13B:
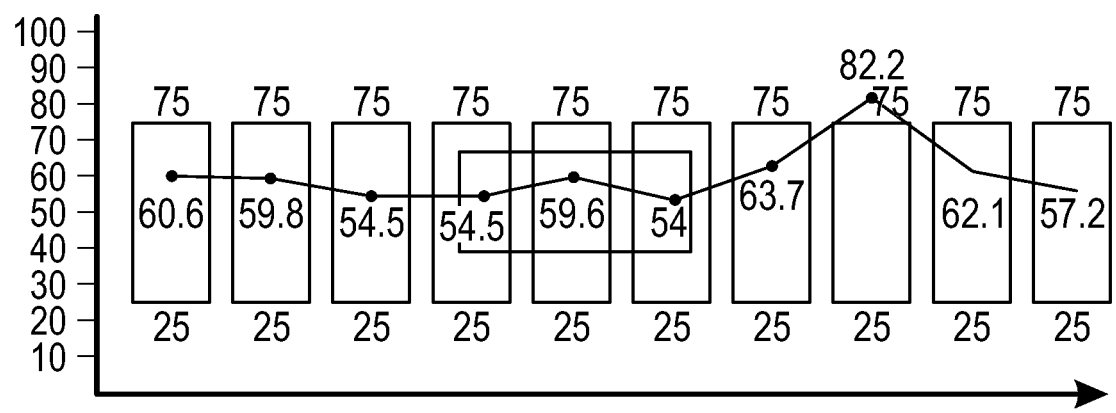

FIGS. 13a and 13b illustrate an example of homogenisation of the ranges of normality within a same laboratory, owing to a change of examination procedure, according to a method of the invention, Thus, the creatinine level needs to be related to two different ranges of normality, of which the clinician is not always informed or aware.

Indeed, any methodological change (equipment, method of analysis) occurring in the same laboratory can result, as in this actual example, in an artificial increase in values that can be inadvertently misleading. The 3 values outlined in FIGS. 13a and 13b in order to observe the difference between the initial curve and the homogenised curve, exhibit a quasistability: contrary to the initial graph, the value farthest to the right (98), initially apparently higher than the first on the left (84), being in reality lower (54.03 versus 54.55).

Figure 14A:
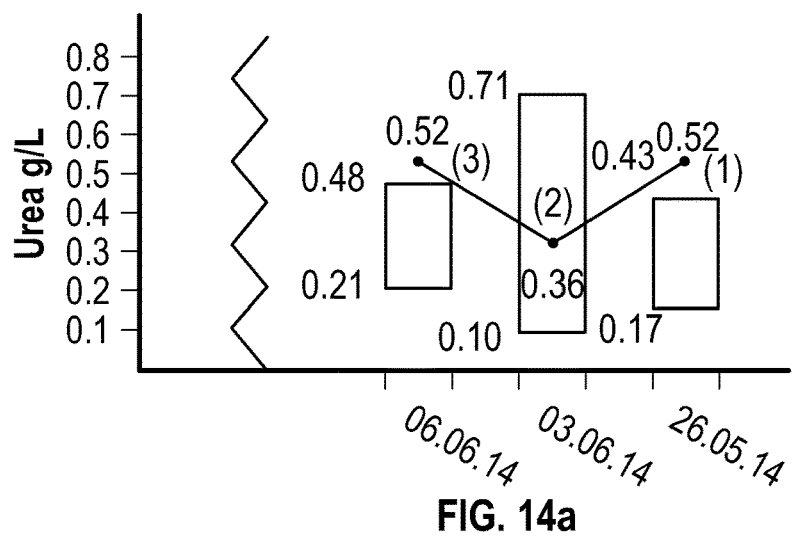
FIGS. 14a, 14b and 14c illustrate homogenisation of the ranges of normality of results expressed in the form of different units, according to the process of the invention.
Figure 14B:
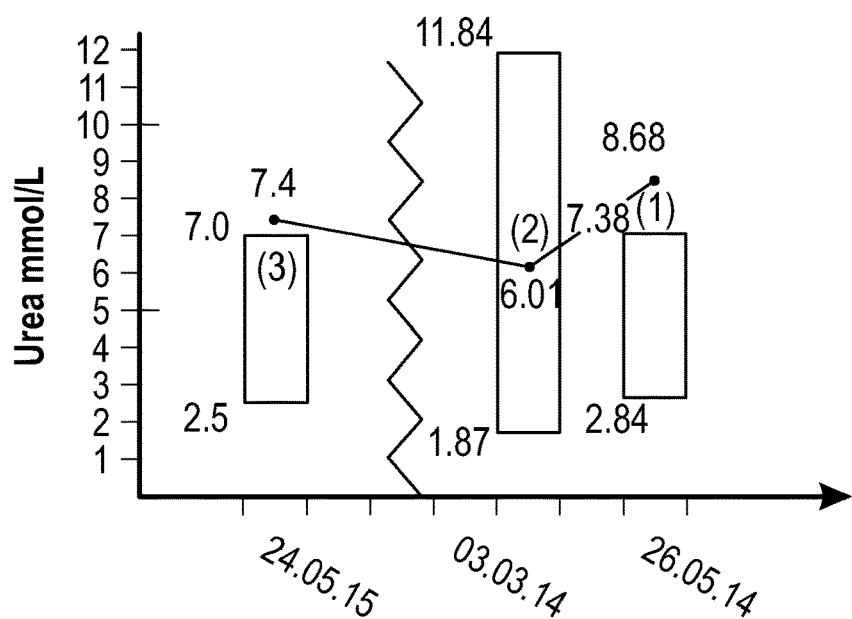
Figure 14C:
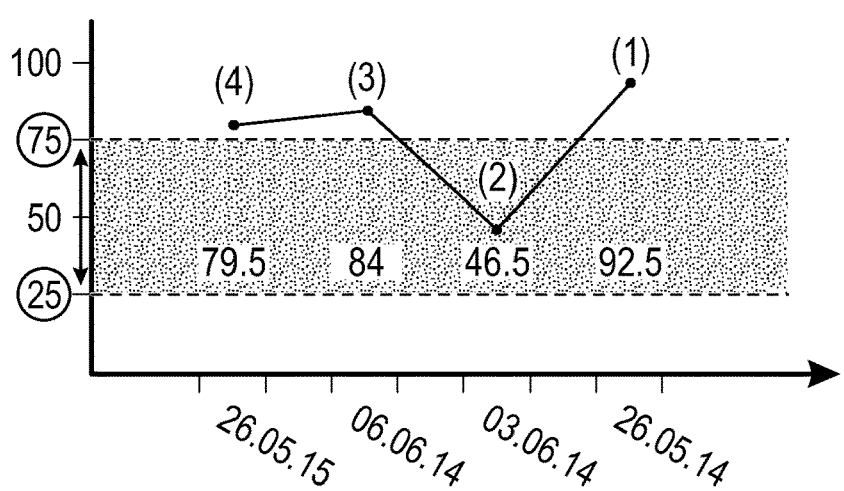

FIGS. 14a, 14b and 14c illustrate homogenisation of the ranges of normality of results expressed in the form of different units, according to a process of the invention. Some laboratories communicate the results of a given test in both units (mmol/L and mg/l), others in a single unit, which makes them non-comparable.

Indeed, a considerable advantage appears in the ability to precisely and accurately compare values of the same test when it is expressed by the laboratory in a unit different from that used by its colleague: for example, the plasma urea level in mmol/l or g/l, as shown respectively in FIGS. 14a and 14b and described in further detail in the respective tables below. FIGS. 14a and 14b also show for each unit of measurement, the normal ranges provided by each laboratory for each measured value.

Over the segment of 4 (actual) values produced for the same patient by four different laboratories, it is observed that the test result of 26 May 2015 is expressed in mmol/only, that of 6 Jun. 2014 in g/L only, whereas the last two, the oldest, are expressed in both units. It is understood that these four results, for the same patient, originate from four different laboratories.

| RENAL FUNCTION | 26.05.2015 | 03.06.2014 | 26.05.2014 |
|---|---|---|---|
| Urea (mmol/L) | 7.4 (2.5-7) | 6.01 (1.67-11.86) | 8.68 (2.84-7.18) |

The above results are presented graphically in FIG. 14b.

| RENAL FUNCTION | 06.06.2014 | 03.06.2014 | 26.05.2014 |
|---|---|---|---|
| Urea (g/L) | 0.52 (0.21-0.48) | 0.36 (0.1-0.71) | 0.52 (0.17-0.43) |

The above results are represented graphically in FIG. 14a.

It is indeed impossible to consolidate these two series of results as they stand, even though they concern the same test and the same patient.

The entire challenge consists in presenting all these results in such a way as to appraise evolution of renal function, whatever the method of expression of results adopted by each laboratory, mmol/l or g/l.

By submitting these data to the method according to the present invention, we obtain an evolutionary diagram, illustrated in FIG. 14c, in which all these values appear without any need to prefer one unit over the other. On the contrary, they are reconciled while maintaining their own unit environment.

This transformation obtained by means of the present invention represents the result of a dual intervention since it eliminates both the (quantitative) differences in the ranges of normality and the fundamental (qualitative) differences in units.

The example described becomes, by selecting for example an upper bound at 75 and a lower bound at 25:

| RENAL FUNCTION | 26.05.2015 | 06.06.2014 | 03.06.2014 | 26.05.2014 |
|---|---|---|---|---|
| Urea (mmol/L) | 7.4 $79.5_{(75-25)}$ $(2.5-7)$ | | 6.01 $46.50_{(75-25)}$ (1.67-11.86) | 8.68 $92.50_{(75-25)}$ (2.84-7.18) |
| Urea (g/L) | | 0.52 $82_{(75-25)}$ (0.21-0.48) | 0.36 $46,495_{(75-25)}$ (0.1-0.71) | 0.52 $92.50_{(75-25)}$ (0.17-0.43) |

The new homogenised values, corresponding to the native measured values, recalculated according to the new range of normality selected (75-25) are shown in italics on the middle line. The data made available to the caregiver are therefore richer.

It will certainly be noted that when the laboratory communicates the result expressed in both units, there may be a slight difference in the calculation between the two homogenised values, related to management of the decimal places, depending on whether the value in mmol/L or the value in g/L is used (46.50 versus 46.495). This remains very limited in terms of its consequences and can be ignored or adjusted by adopting the median between the two to position the point on the graph. On the other hand, this can play an additional quality control role.

This harmonisation of different units is of particular importance in many clinical situations, with the knowledge that a "chronic" patient is generally monitored by two or even three (or more) practitioners who generally work with different laboratories (general practitioner and specialists in private practice, hospital physician). This provides all those involved with an exhaustive and accurate view of evolution of the case, as indicated by these biological results.

Figure 15A:
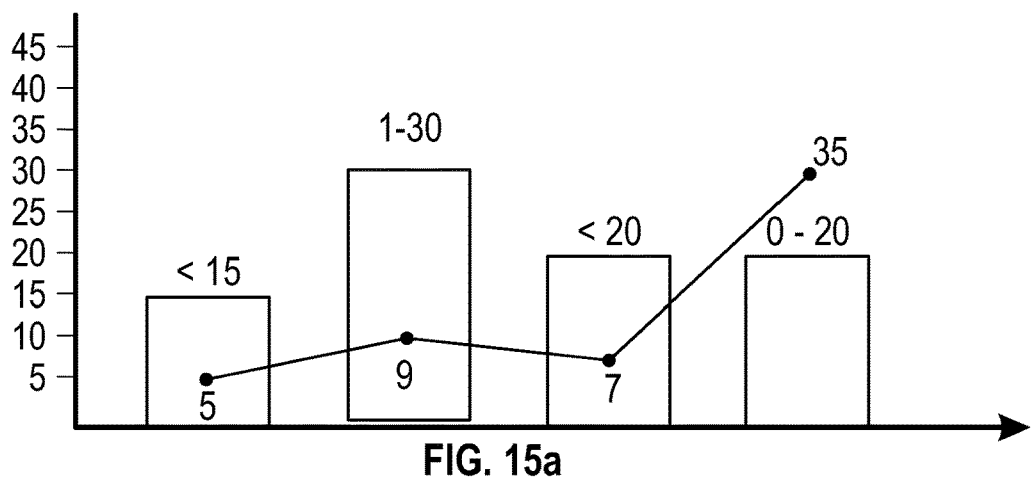
FIGS. 15a and 15b illustrate homogenisation of the ranges of normality of the results when the biological analysis laboratory or laboratories stipulate(s) that the range of normality is either "less than or equal to" or "strictly less than" an upper bound of normality, or that it is included within a range limited by an upper bound of normality and a lower bound of normality.
Figure 15B:
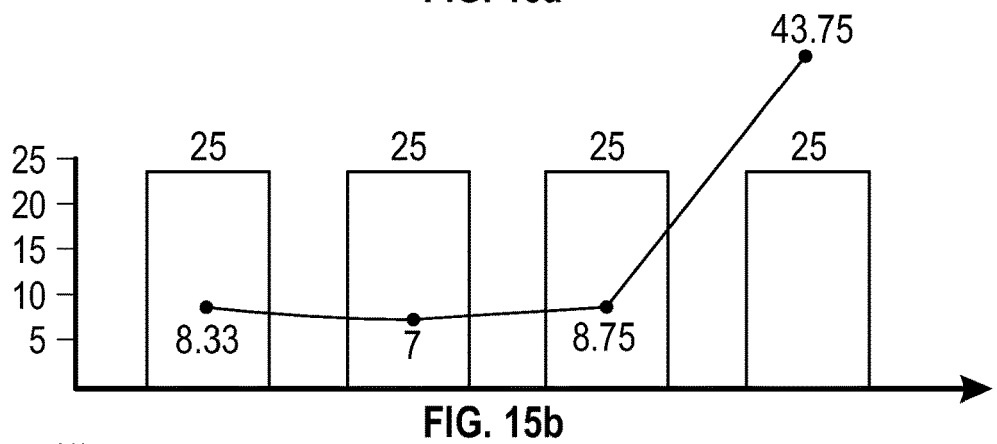

FIGS. 15a and 15b illustrate an example of homogenisation of the ranges of normality of results. When the biological analysis laboratories stipulate for example that the range of normality is "less than or equal to" or "strictly less than" a higher bound of normality and/or the range of normality is included between two values, the representation in FIG. 15a can be obtained. FIG. 15b then illustrates the graphic representation with a range of normality homogenised according to the invention.

Figure 15C:
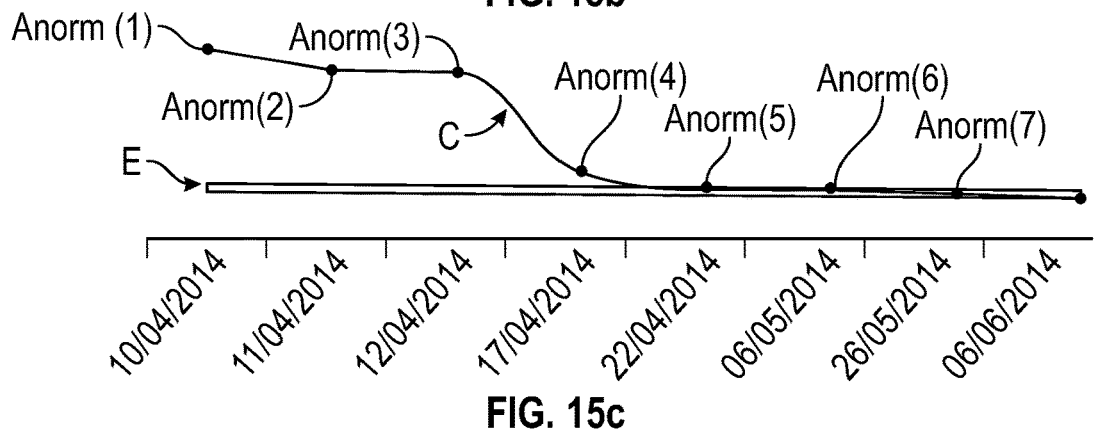
FIGS. 15c and 15d illustrate homogenisation of the ranges of normality with two examples of graphic representation corresponding to two methods of implementing the method according to the invention.
Figure 15D:
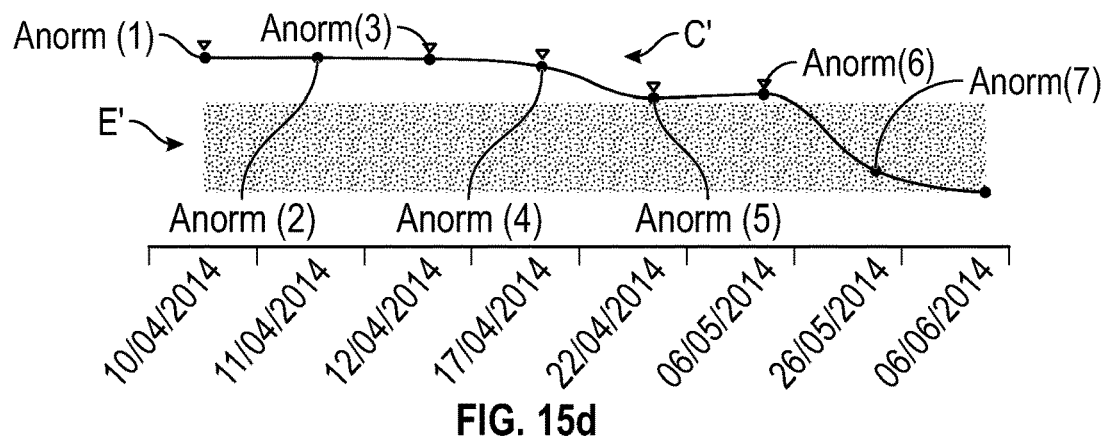

FIGS. 15c and 15d illustrate homogenisation of the ranges of normality with two examples of graphic representation corresponding to two methods of implementing a method according to the invention.

Thus, according to an embodiment, a method of the invention consists in, when at least one value A(n) is greater than or equal to its associated bound of normality BS(n):

calculating the linear correlation coefficient for each initial value A(n), using the following equation:

$$Cbs(n)=(A(n)-BS(n))/(BS(n)-BI(n))$$

or $$Cbi(n)=(A(n)-BI(n))/(BS(n)-BI(n))$$

and subsequently calculating for said value A(n) greater than or equal to its associated bound of normality BS(n), the normalised value Anorm(n), using the following equation:

$$Anorm(n)=BSnorm+Ln(Cbs(n)\times(BSnorm-BInorm))$$

or $$Anorm(n)=BInorm+Ln(Cbi(n)\times(BSnorm-BInorm))$$

where BInorm and/or BSnorm are respectively the common lower and/or upper bounds of normality of the common normalised normal range.

It is possible in this case to optimise display of the results of analyses performed on different dates, as it is shown in FIGS. 15c and 15d. The different measurement points are connected to each other to form a curve C and are positioned in relation to a homogenised range E of normality according to the invention in FIG. 15c. In this example however, some values A(n), namely A(1), A(2), A(3), A(4), A(5) and A(6) are higher than the corresponding upper bounds of normality BS(n). Some of these values may be much higher than the other values. This would result in flattening of the homogenised range of normality E as shown in FIG. 15c. The representation of the curve C would be more difficult to read in this case and could result in loss of data.

On the other hand, according to an embodiment of a method according to the invention described above, using the logarithm function (Napierian or decimal) for processing the values A(1) to A(6), another representation of the curve C and the homogenised range of normality E is obtained; namely the curve C' and the homogenised range of normality E' in FIG. 15d. Advantageously, the values A(1) to A(6) are marked with a sign, for example a triangle, to inform the reader that they have undergone logarithmic processing. It is apparent in this case that the representation in FIG. 15d is much easier to read and understand and moreover without any loss of data.

According to another embodiment, a method of the invention consists in, when at least one value A(n) is less than or equal to its associated bound of normality BI(n):

calculating the linear correlation coefficient for each initial value A(n), using the following equation:

$$Cbs(n)=(A(n)-BS(n))/(BS(n)-BI(n))$$

or $$Cbi(n)=(A(n)-BI(n))/(BS(n)-BI(n))$$

and subsequently calculating for said value A(n) less than or equal to its associated bound of normality BI(n), the normalised value Anorm(n), using the following equation:

$$Anorm(n) = BSnorm - Ln(-Cbs(n) \times (BSnorm - BInorm))$$

or $$Anorm(n) = BInorm - Ln(-Cbi(n) \times (BSnorm - BInorm))$$

where BInorm and/or BSnorm are respectively the common lower and/or upper bounds of normality of the common normalised normal range.

Furthermore, in addition to the two preceding paragraphs, the method according to the invention consists in, when a value A(n) is on the one hand less than or equal to its associated bound of normality BS(n) and on the other hand greater than or equal to its associated bound of normality BI(n):

calculating the linear correlation coefficient for each initial value A(n), using the following equation:

$$Cbs(n) = (A(n) - BS(n))/(BS(n) - BI(n))$$

or $$Cbi(n) = (A(n) - BI(n))/(BS(n) - BI(n))$$

and subsequently calculating for said value A(n) less than or equal to its associated bound of normality BS(n) and greater than or equal to its associated bound of normality BI(n), the normalised value Anorm(n), using the following equation:

$$Anorm(n) = BSnorm + Cbs(n) \times (BSnorm - BInorm)$$

or $$Anorm(n) = BInorm + Cbi(n) \times (BSnorm - BInorm)$$

where BInorm and/or BSnorm are respectively the common lower and/or upper bounds of normality of the common normalised normal range.

FIGS. 15c and 15d and their related explanations can be very easily transposed to this other method of implementing a method according to the invention in which at least one A(n) value is lower than its lower bound of normality BI(n).

The other values A(n), located within the normal range BI(n)–BS(n), do not undergo any logarithmic processing as specified above.

Figure 16:
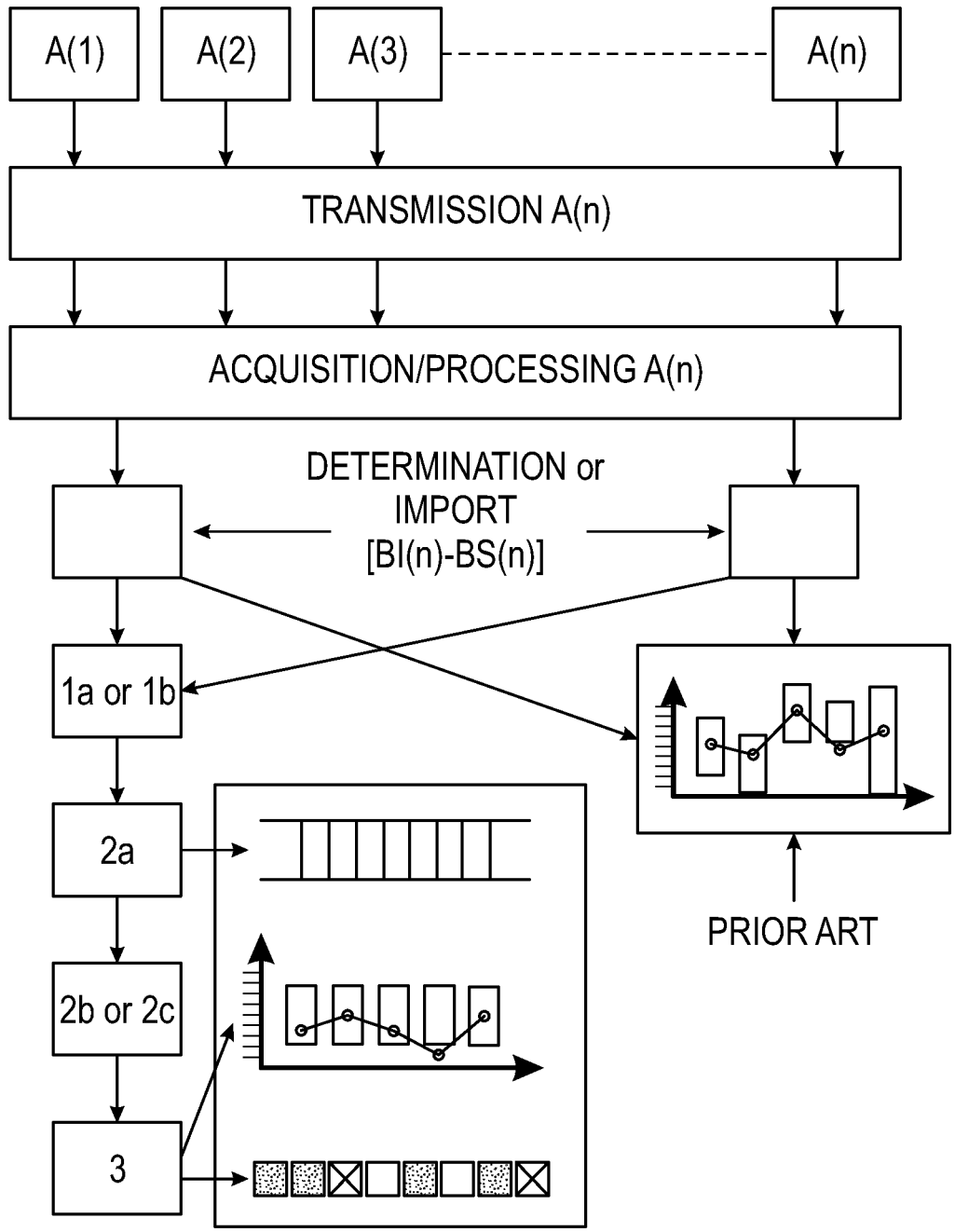
FIG. 16 illustrates with a functional flowchart a general embodiment of the method according to the invention.

FIG. 16 illustrates with a functional flowchart an embodiment of a method according to the invention. This flowchart illustrates the parts of a method according to the invention, which are identified in particular in FIG. 4.

FIGS. 17a, 17b, 17c, 17d, and 17e illustrate examples of possible intuitive representations of results of analysis by means of the method according to the invention.

This results in several proposals that illustrate a method according to the invention.

Figure 17A:
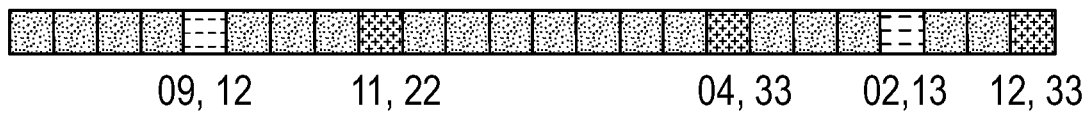
FIGS. 17a, 17b, 17c, 17d, 17e illustrate examples of possible intuitive representations of results of analysis by means of the method according to the invention

The first proposal illustrated in FIG. 17a takes the form of a continuous line consisting of an assembly of squares (or other geometric shapes) of different colours according to the measured value that they represent, each corresponding to a test. The progression is chronological. The colour chart follows the usual pattern, green (hatching) for normal values, red (+ signs) for abnormally high values, blue (− signs) for abnormally low values and a white square when the result is not interpretable, no data being transmitted.

A single text element, i.e. the date of the most recent examination and possibly the dates corresponding to abnormal values are indicated, either permanently or ephemerally at the user's request.

Figure 17B:
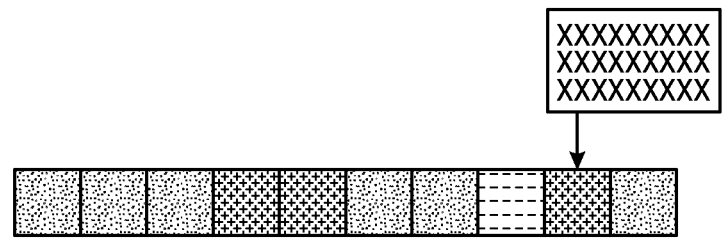

They may also not be directly visible, such as those of the "normal" green squares and may only appear in the form of ephemeral metadata, illustrated in FIG. 17b, when the area is prompted. In this case, as in the previous graphs, an indication of the laboratory of origin, the measured value and the corresponding normality interval will also appear.

Figure 17C:
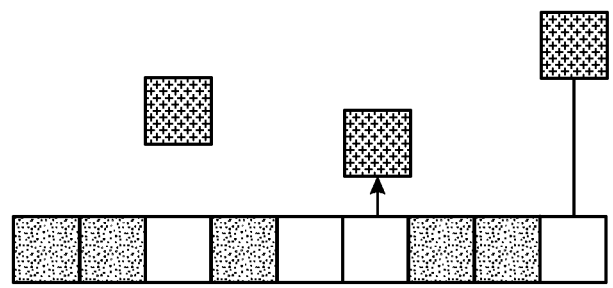

The third proposal, illustrated for example in FIG. 17c, maintains the same principle of single representation, by a green square (hatching), of any value within the range of normality, whatever said value may be. Squares of different colours(s) (+ signs inside the square) are also used for abnormally high or low values. For the latter however, this proposal provides purely visual quantitative data by moving the square away from the baseline, in proportion to the distance between the measured value and normality.

Figure 17D:
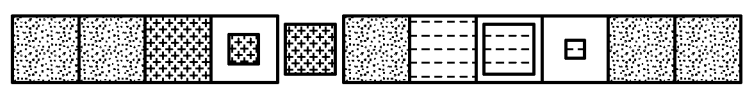

In order to avoid widening the field excessively, the fourth proposal, illustrated in FIG. 17d, plays on the size of the squares. The degree of reduction is proportional in this case to the distance of the normal values without their position moving away from the baseline. If a barely perceptible "point" results, one can use artifice such as construction of an empty square of the appropriate colour, red or blue, of which only the outlines are displayed and in the centre of which the so-called "minimal" representation will appear.

Figure 17E:
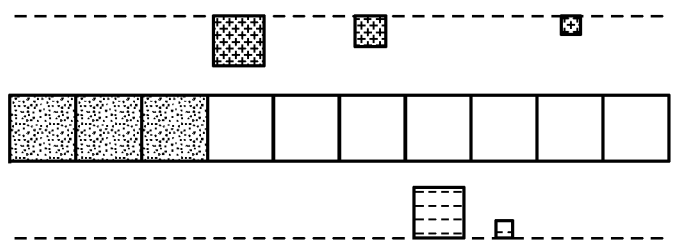

Both types of representation may also be combined, as illustrated in FIG. 17e for example, by fixing a constant spacing in relation to the baseline and subsequently placing the red or blue squares, the size of which is representative of the distance from the normal values, respectively at the top and bottom on two parallel lines close to the baseline.

In the context of the present invention, the essential question is that of communication of the collected data, with the aim of making the latter available to the nursing personnel or the patient in the most effective way.

In addition, there is a desire to adapt to new electronic data consultation tools such as tablets, smartphones and other connected objects such as watches. The reading format must be closely adapted to the consultation medium.

With that in mind, the present patent has also sought maximum simplification of the graphic representation while maintaining the accuracy and completeness of the data, by allowing, if the observer desires, retrieval of the data in their entirety in the form of metadata and "backtracking" to untransformed values or even to the initial table preceding any graphic translation.

It is therefore possible to opt, by way of an example of embodiment, for simplification that comprises several degrees, for instance:

1) no numerical indication other than that defining the date of the examination 2) use of colorimetric indexes: green for normality, red for an abnormal measured value by excess, blue for an abnormal measured value by default, 3) chronological representation according to a parameterisable "timeline", 4) use of the tablet/smartphone 90° image rotation function to provide a different view, graph or spreadsheet, in portrait or landscape format, 5) visually intuitive expression of the measured values according to a gradation of the risk (by changing the shape, size, frame of the representative image, 6) graphic interpretation of the notion of distance (in order to avoid excessive distance from the "baseline"", 7) possible absence of any visual identification of the origin of the laboratory that carried out the examination, 8) timely availability of all the complete data in the form of ephemeral metadata—when the target is prompted by the mouse pointer or touch.

Many other representations are possible by upholding the principle of pure graphic representation and non-discrimination of values located within the range of normality.

These deliberately simplified representations always contain all the data in the "background" in the form of ephemeral metadata. They are mainly intended for patients or can serve as pre-programmed alerts for caregivers to appear on a mobile terminal of the telephone or smart watch type or any connected object suitable for this purpose.

The most condensed form consists in solely communicating the abnormal test(s), with all those that fall within the normality interval appearing in the most elementary form, either a single geometric figure (square or dot, green for example) or by only their heading appearing in green.

Finally, a chronological presentation of the last 3, 5 (or X) results can be displayed in the same form of coloured representations allowing monitoring of the evolutionary profile, whereby a checkbox opens to display all the historical results for this test.

Figure 18:
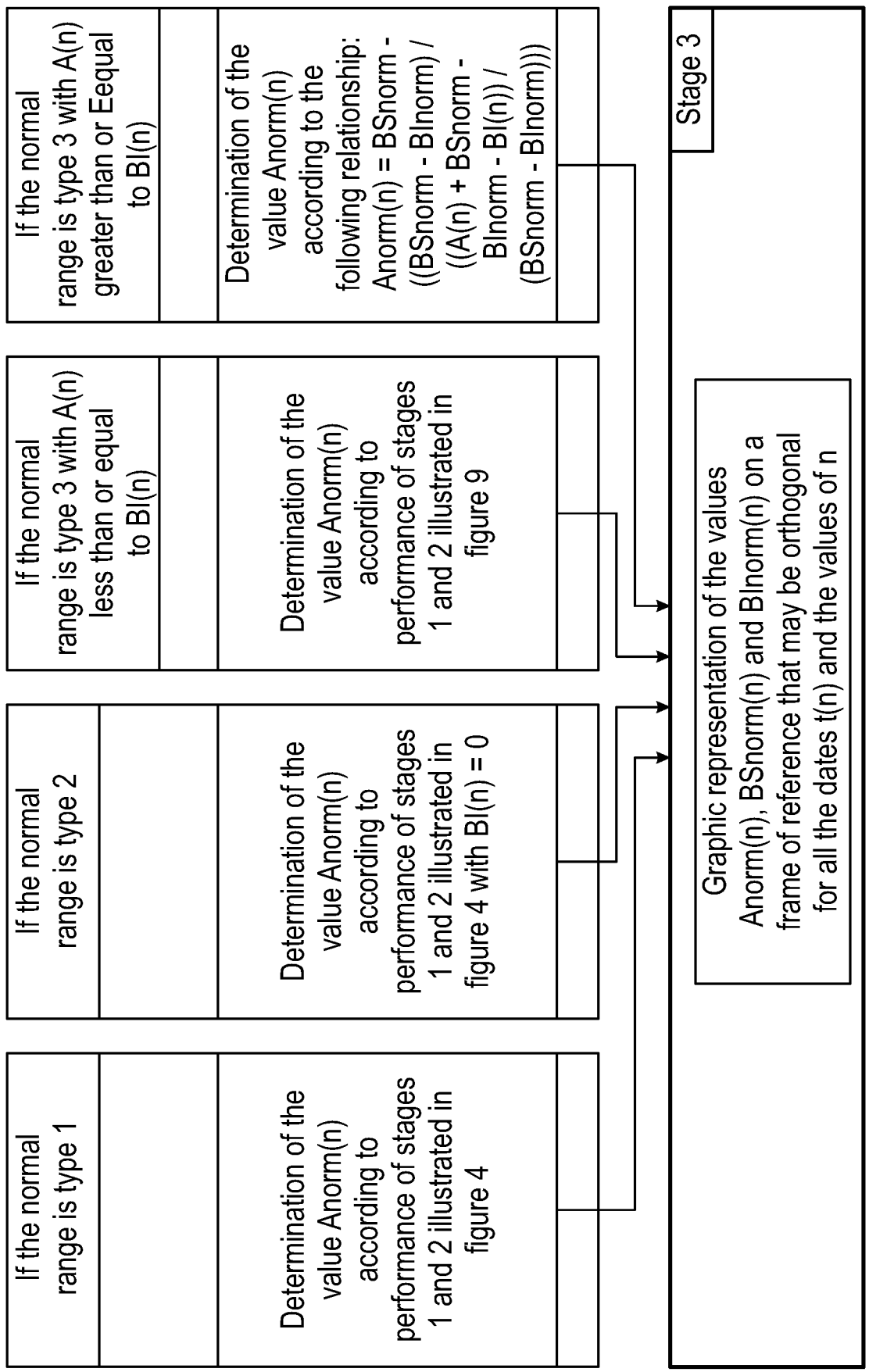
FIG. 18 illustrates using another flowchart the main stages of the method according to the invention within the context of a specific case in which at least one of the measured values A(n), but not all the measured values, is associated with a normal range solely delimited by a lower bound of normality BI(n)

FIG. 18 illustrates with a flowchart the three main stages of the method according to the invention within the context of a specific case in which the ranges of normality (or the normal ranges) associated with the measured values A(n) similar and to be compared are of three different types:

Type 1: When the range of normality is defined by the association of a lower bound of normality BI(n) and an upper bound of normality BS(n).

Type 2: When the range of normality is "less than or equal to" or "strictly less than" an upper bound BS(n).

Type 3: When the range of normality is "greater than or equal to" or "strictly greater than" a lower bound BI(n).

Figure 19:
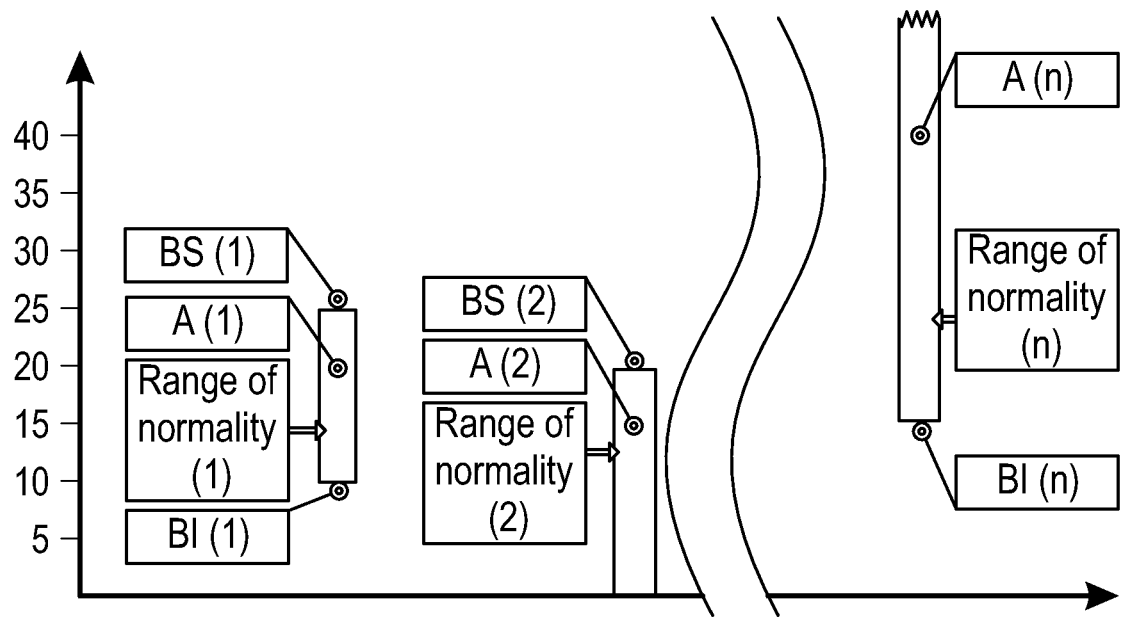
FIGS. 19 and 20 illustrate the graphic result of application of the method according to the invention in FIG. 18 to a sequence of measured values A(n) associated with their respective normalised normal ranges (FIG. 19) and obtaining of a common normalised upper bound BSnorm for all said measured values A(n).
Figure 20:
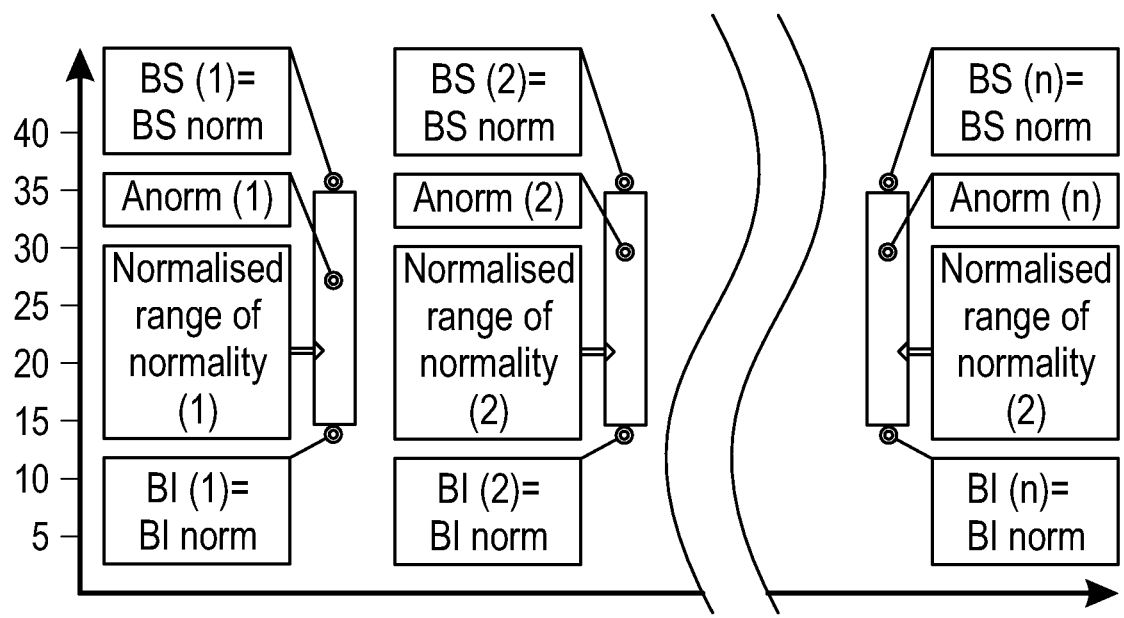

This specific case is illustrated in FIGS. 18, 19 and 20.

A method according to the invention, involving transformation and representation for all the values A(n) to be compared falling within category type 1, is presented in the detailed description of FIGS. 4, 5 and 6.

A method according to the invention, involving transformation and representation for all the values A(n) to be compared falling within category type 2, is presented in the detailed description of FIGS. 7 and 8.

Regarding the measured values A(n) falling within category type 3, a method according to the invention involving transformation and representation for all the values A(n) to be compared presented in the detailed description of FIGS. 9, 10 and 11, is not entirely suitable, since the respective upper bounds of normality BS(n) are equal to infinity and cannot be normalised by a finite value BSnorm as is possible in the case of the values A(n) falling within category type 1 and 2.

Hence, for the values A(n) falling within category type 3, we propose that if the value of A(n) is less than or equal to the value of the lower bound of normality BI(n) of its associated range of normality, the method according to the invention involving transformation and representation, presented in the detailed description of FIGS. 9, 10 and 11 be applied.

In the event that the A(n) value falling within category type 3 is greater than or equal to the value of the lower bound of normality BI(n) of its associated range of normality, we propose that a method according to the invention involving transformation and representation, based on a mathematical model that fulfils the following condition, be applied:

For any A(n) value included between BI(n) and infinity, Anorm(n) will always be "strictly less than" or "less than or equal to" the chosen BSnorm value.

According to an embodiment of a method according to the invention, for any A(n) belonging to category type 3, the value of which is greater than the value of the bound of normality BI(n) of its associated range of normality, the following equation is used:

$$A\text{norm}(n) = B\text{Snorm} - ((B\text{Snorm} - B\text{Inorm})^2 / (A(n) + B\text{Snorm} - B\text{Inorm} - BI(n)))$$

The method according to the invention is remarkable in that it allows in particular use of all the raw initial values A(n), without prior processing or transformation and moreover independently of the fact that these values A(n) are each defined in relation to a finite range of normality delimited by an upper bound BS(n) and a lower bound BI(n)) or simply in relation to a single lower bound BI(n) or upper bound BS(n), without any detriment to the homogeneity of the values Anorm(n) thus obtained.

Obtaining results involves specific means including a computer hardware unit, a set of application software, a storage base supplied by secure channels, an algorithmic calculation program, a tabular or graphic display engine and a display terminal of any type, cathodic, LED, LCD, . . . . In addition to the variants on each workstation described, massive data processing tools and APIs for specific applications are also available.

By way of example, a computer program serves to transform the initial values A(n) into normalised values Anorm (n). This same computer program can also be used to determine or help determine, by calculation for instance, the normalised upper bound BSnorm and lower bound BInorm of the normalised normal range.

It is clear that the present description is not restricted to the examples explicitly described, but also includes other embodiments and/or implementation. Hence, a described stage of embodiment of the method according to the invention can be replaced with an equivalent stage without going beyond the ambit of the invention.

The invention claimed is:

1. A method for tracking a biological parameter of a patient by processing one or more initially-measured values A(n) that correspond to results of one or more biological analyses of the patient's biological parameter from one or more laboratories, the method comprising:

a) receiving, by a computer processor, health data sent by a messaging system, wherein the health data originates in a first encoded format and a second encoded format from a plurality of laboratories and includes at least one initial value A(n) and metadata indicating a corresponding normal range, wherein the first encoded format and the second encoded format are different encoded formats, wherein the at least one initial value, A(n), is measured on a given date and expressed by a given laboratory among the plurality of laboratories according to a unit of measurement proposed by said given laboratory, and wherein the normal range (BI(n), BS(n)) is provided by the same laboratory corresponds to an analysis methodology that defines the conditions of the analysis by which the at least one initial value was obtained on the given date, and is delimited by a lower bound BI(n) and an upper bound BS(n), by a range lower than the upper bound BS(n) only, or by a range higher than the lower bound BI(n) only;

b) recording, by the computer processor, the health data from the plurality of laboratories as consolidated data on a server;
c) transforming, by the computer processor using the consolidated data, each of the initial values A(n) into a normalized value Anorm(n), through the use of a mathematical model and computer processing,
wherein the normalized value Anorm(n) is defined relative to a common scale (0, 100) of homogenized values;
d) determining, by the computer processor, a common normalized normal range (BInorm, BSnorm) in relation to the common scale (0, 100) of homogenized values,
wherein the common normalized normal range is defined by a common simple normalized lower bound BInorm, by a common simple normalized upper bound BSnorm, or by a range delimited by the common normalized upper bound BSnorm and the common homogenised lower bound BInorm; and
e) generating and displaying, by the computer processor and using an electronic graphical representation, a progression over time of the given biological parameter by means of the normalized values Anorm(n),
wherein the normalized values Anorm(n) are presented in combination with at least one element of data, that relates to the common normalized normal range (BInorm,BSnorm),
wherein the mathematical model of (c) comprises
when a value A(n) is on the one hand less than or equal to its associated bound of normality BS(n) and on the other hand greater than or equal to its associated bound of normality BI(n),
performing calculation of the linear correlation coefficient for each initial value A(n) using the equation:

$Cbs(n)=(A(n)-BS(n))/(BS(n)-BI(n))$ or $Cbi(n)=(A(n)-BI(n))/(BS(n)-BI(n))$ where BI(n) and BS(n) are respectively the finite lower and upper bounds of normality of the normal range in relation to the initial value A(n);
calculating the normalized values Anorm(n) using the equation:

$Anorm(n)=BSnorm+Cbs(n)\times(BSnorm-BInorm)$ or $Anorm(n)=BInorm+Cbi(n)\times(BSnorm-BInorm)$ where BInorm and/or BSnorm are respectively the common lower and/or upper bounds of normality of the common normalized normal range;
when the bound of normality BS(n) is infinite, calculating a linear correlation coefficient Cb0(n) based on the lower bound of normality BI(n) and the initial value A(n) and on the difference between the lower bound BI(n) and the origin 0, by calculating the linear correlation coefficient for each initial value A(n), using the equation:

$Cb0(n)=(A(n)-0)/(BI(n)-0)$ where BI(n) is the lower bound of normality in relation to the initial value A(n), with BS(n) being an infinite value,
and calculating the normalized values Anorm(n) using the equation:

$Anorm(n)=BInorm+(Cb0(n)\times(BInorm-0))$ where BInorm is the common normalized lower bound of normality of the common normalized normal range.

2. The method according to claim 1, further comprising, when at least one value A(n) is greater than or equal to its associated bound of normality BS(n):
calculating the linear correlation coefficient for each initial value A(n), using the equation:

$Cbs(n)=(A(n)-BS(n))/(BS(n)-BI(n))$ or $Cbi(n)=(A(n)-BI(n))/(BS(n)-BI(n))$ and subsequently calculating for said value A(n) greater than or equal to its associated bound of normality BS(n), the normalized value Anorm(n), using the equation:

$Anorm(n)=BSnorm+Ln(-Cbs(n)\times(BSnorm-BInorm))$ or $Anorm(n)=BInorm+Ln(-Cbi(n)\times(BSnorm-BInorm))$ where BInorm and/or BSnorm are respectively the common lower and/or upper bounds of normality of the common normalized normal range.

3. The method according to claim 1, further comprising, when at least one value A(n) is less than or equal to its associated bound of normality BI(n):
calculating the linear correlation coefficient for each initial value A(n), using the equation:

$Cbs(n)=(A(n)-BS(n))/(BS(n)-BI(n))$ or $Cbi(n)=(A(n)-BI(n))/(BS(n)-BI(n))$ and subsequently calculating for said value A(n) less than or equal to its associated bound of normality BI(n), the normalized value Anorm(n), using the equation:

$Anorm(n)=BSnorm-Ln(-Cbs(n)\times(BSnorm-BInorm))$ or $Anorm(n)=BInorm-Ln(-Cbi(n)\times(BSnorm-BInorm))$ where BInorm and/or BSnorm are respectively the common lower and/or upper bounds of normality of the common normalized normal range.

4. The method according to claim 1, further comprising selecting the highest value upper bounds of normality BS(n) that is provided by the plurality laboratories, and/or selecting the lowest value lower bounds of normality BI(n) that is provided by the plurality of laboratories, in order to determine respectively the upper bound of normality BSnorm and the lower bound of normality BInorm.

5. The method according to claim 1, further comprising determining the common normalized normal range (BInorm, BSnorm) by calculating the arithmetic mean over the values of all the normal ranges (BI(n),BS(n)) provided by the plurality of laboratories for the same measured biological test, without taking into account the respective positioning of the different BI(n) and BS(n) but only the intervals between the latter.

6. The method according to claim 1, further comprising determining the common normalized upper bound of normality BSnorm by calculating the arithmetic mean of all the values of the upper bounds of normality BS(n) followed by that of the common normalized lower bound of normality BInorm by taking as the basis all the values of the lower bounds of normality BI(n), wherein the operation may also be performed by taking as the basis a limited number of these selectively chosen bounds BI(n) and/or BS(n).

7. The method according to claim 1, further comprising, when at least one value A(n) is associated with a normal range having only a lower bound of normality BI(n), BS(n) being an infinite value,
 e1) on the one hand, when the value of A(n) is less than or equal to the value of BI(n), calculating a linear correlation coefficient Cb0(n) based on the lower bound of normality BI(n) and the initial value A(n) and on the difference between the lower bound of normality BI(n) and the origin 0, by calculating the linear correlation coefficient for each initial value A(n), using the equation:

$Cb0(n)=(A(n)-0)/(BI(n)-0)$ and calculating the normalized values Anorm(n), using the equation:

$Anorm(n)=BInorm+(Cb0(n) \times (BInorm-0))$ e2) and on the other hand, when the value A(n) is greater than or equal to the value of BI(n), calculating the normalized value Anorm(n) using a mathematical equation verifying the condition that if the value of A(n) is between BI(n) and infinity, then Anorm(n) will be less than the value adopted for the normalized upper bound of normality BSnorm, thereby associating all the values Anorm(n) with a common normalized normal range (BInorm, BSnorm).

8. The method according to claim 1, further comprising, under e2), using the equation:

$Anorm(n)=BSnorm-((BSnorm-BInorm)^2/(A(n)+BSnorm-BInorm-BI(n)))$.

9. The method according to claim 1, comprising the steps of displaying a graph on which the corresponding dates and results of the analyses (n) for the same test and the same patient are plotted along a horizontal axis, in chronological order, and on the other hand, along a vertical axis, for all these analyses, wherein the single common normalized normality range (BInorm, Bsnorm) associated with normalized values Anorm(n), the positions of the different neighbouring normalized values Anorm(n) are connected by line segments ranging from one normalized value Anorm(n) to the next Anorm (n+1), while the single common normalized normality range (BInorm, Bsnorm) is represented in the form of a vertical rectangle or any other geometrical line or materialisation representative of this normalized range of normality.

10. The method according to claim 1, comprising the step of defining on a location area of each normalized value Anorm(n), an active area, which when pointed to or selected by means of a mouse or any other instrumental or digital action, makes it possible to display a window containing at least some of the data forming the metadata attached to the measured value A(n).

11. The method according to claim 1, further comprising importing additional medical data from a patient's personal electronic medical record (PEMR), in order to complete the graphic representation at the request of health personnel, by combining different types of medical data from clinical diagnostic, imaging registers or therapeutic registers in order to create tables of preferences corresponding to uses and needs of caregivers for optimal patient management.

12. The method according to claim 1, further comprising consolidating comparable data between a number of patients in order to create a silo of data that is rendered anonymous without possible recovery of individual identities.

13. The method according to claim 1, further comprising formatting previously incompatible data, either for a single patient or for multiple patients, through the use of homogenized values.

\* \* \* \* \*